United States Patent [19]
Hansen

[11] Patent Number: 5,286,452
[45] Date of Patent: Feb. 15, 1994

[54] SIMULTANEOUS MULTIPLE ASSAYS

[75] Inventor: W. Peter Hansen, New York, N.Y.

[73] Assignee: Sienna Biotech, Inc., New York, N.Y.

[21] Appl. No.: 883,574

[22] Filed: May 15, 1992

Related U.S. Application Data

[63] Continuation-in-part of Ser. No. 702,302, May 20, 1991, abandoned.

[51] Int. Cl.$^5$ ............................................. G01N 15/02
[52] U.S. Cl. .................................... 422/73; 422/82.05; 422/82.09; 435/808; 436/523; 436/533; 436/534; 436/805; 356/336; 356/338
[58] Field of Search ................... 422/73, 82.05, 82.09; 436/164, 517, 805, 165, 807, 533, 523, 534; 435/7.1, 805, 808; 356/336, 338

[56] References Cited

U.S. PATENT DOCUMENTS

| | | | |
|---|---|---|---|
| 5,144,224 | 9/1992 | Larsen | 324/71.4 |
| 5,162,863 | 11/1992 | Ito | 356/73 |
| 5,198,369 | 3/1993 | Itoh et al. | 436/534 |

Primary Examiner—James C. Housel
Assistant Examiner—Long V. Le
Attorney, Agent, or Firm—Rothwell, Figg, Ernst & Kurz

[57] ABSTRACT

A particle agglutination-based, stable kinetic method for simultaneously determining the concentrations of multiple analytes in a single fluid sample with the addition of a single reagent, that entails the use of a novel high resolution sheath flow cell, a novel optical flow particle analyzer (FPA), and unidirectional low angle forward light scattering from multiply-sized or refractive indexed, differently coated particles and their aggregates. Also disclosed are two embodiments of an instrument specifically designed to carry out the method of the invention.

24 Claims, 18 Drawing Sheets

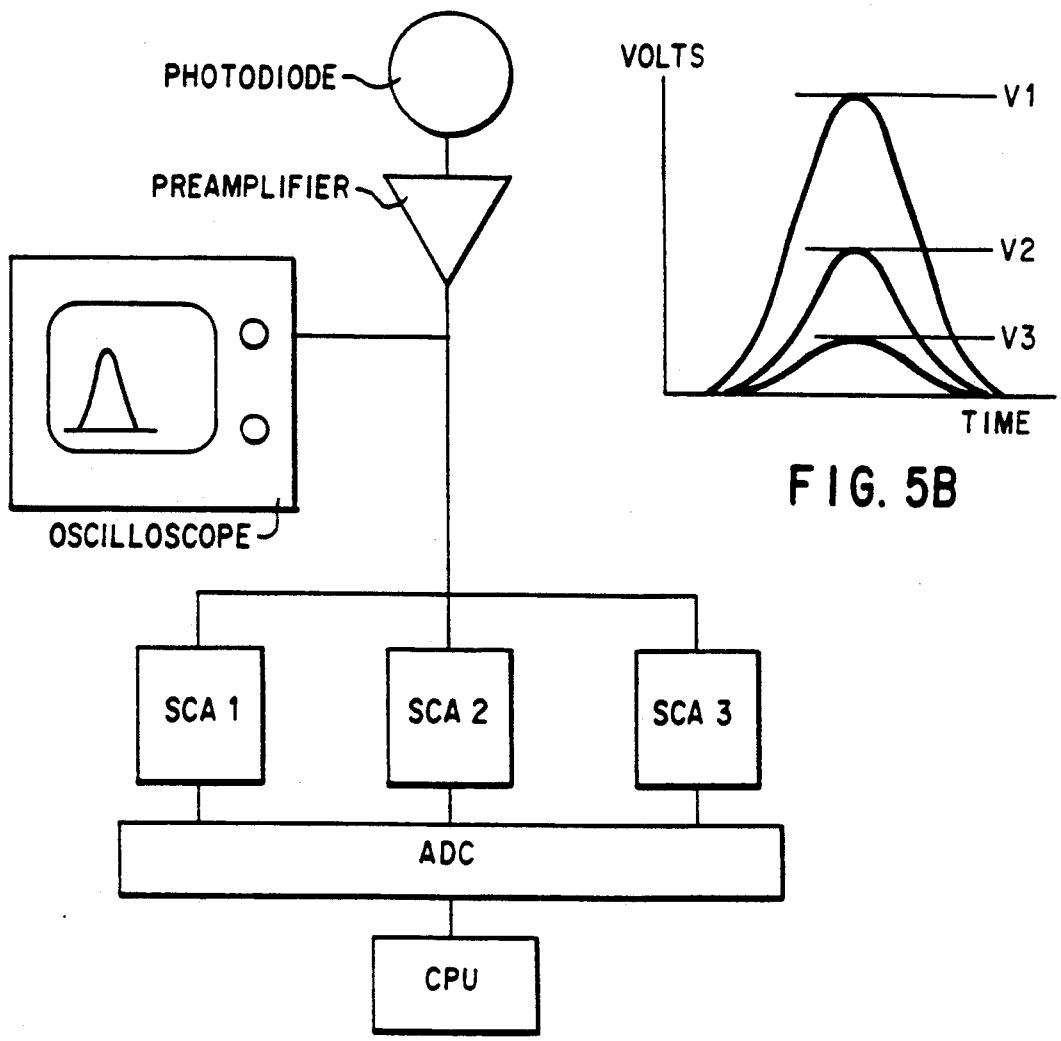
FIG. 5A
FIG. 5B
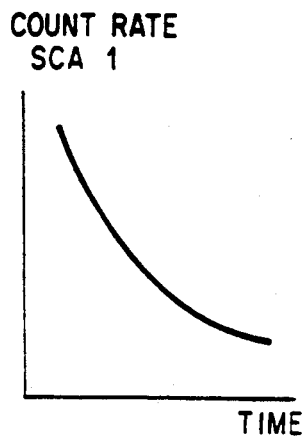
FIG. 5C
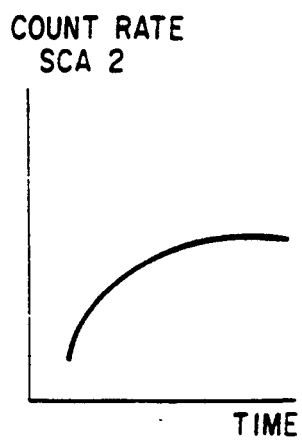
FIG. 5D
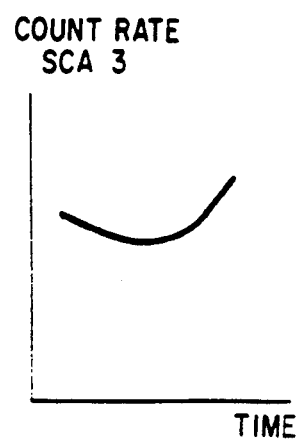
FIG. 5E

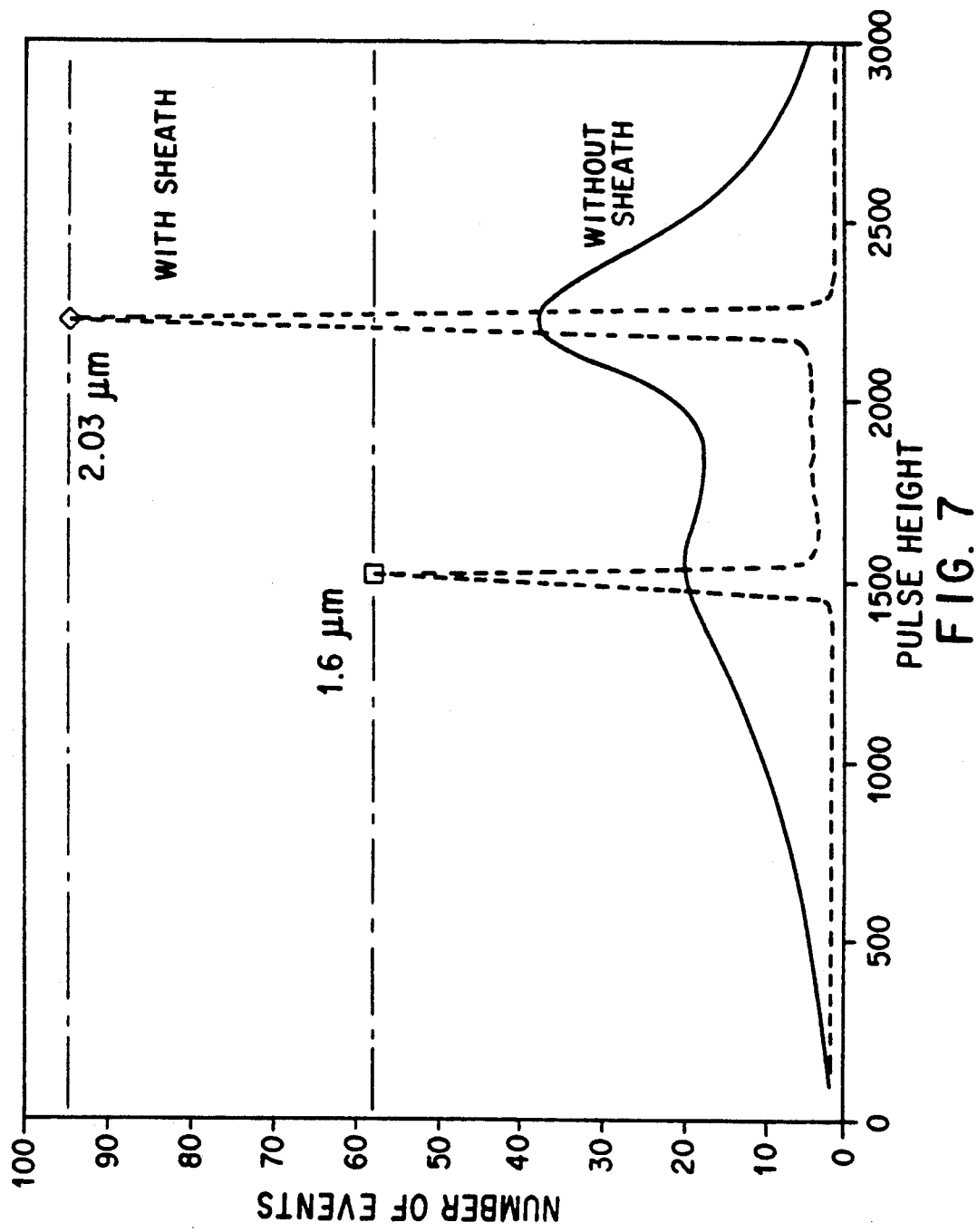

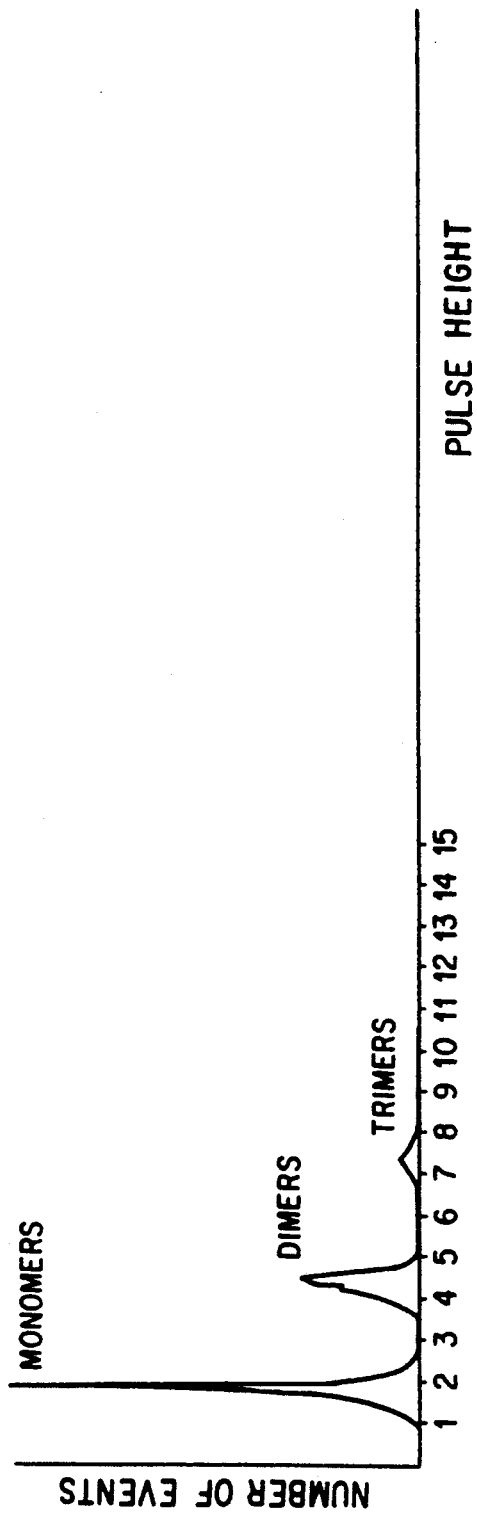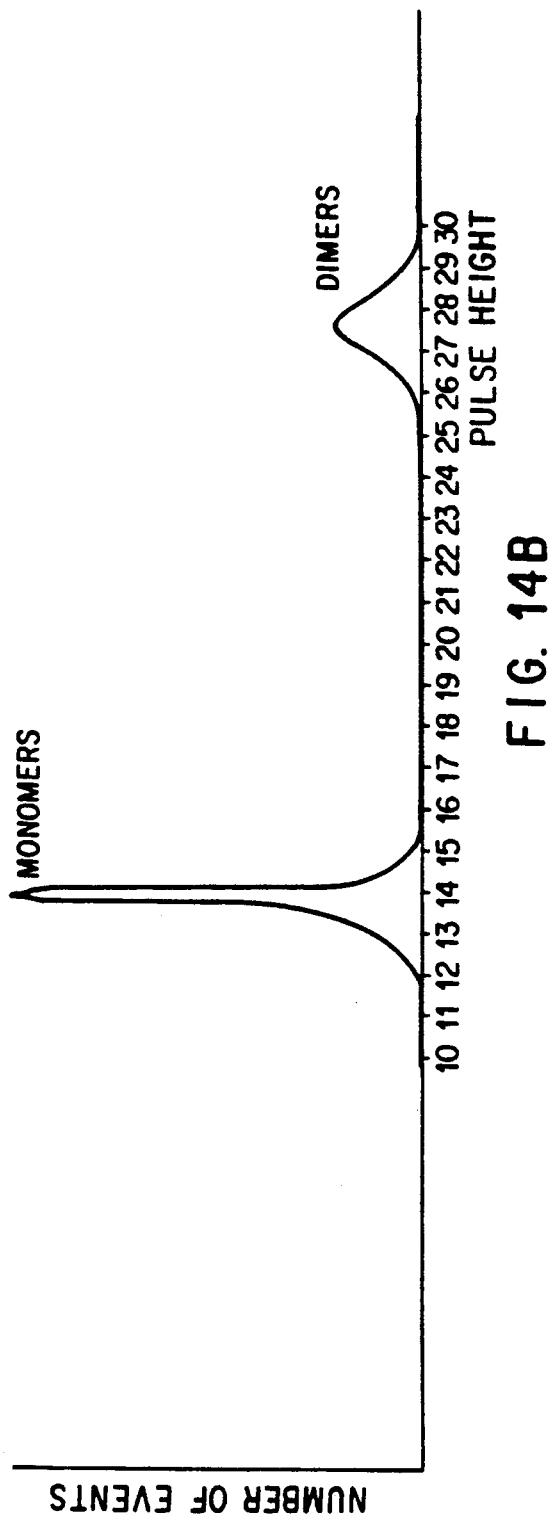

SIMULTANEOUS MULTIPLE ASSAYS

This is a continuation-in-part of Ser. No. 07/702,302, filed May 20, 1991, now abandoned.

FIELD OF THE INVENTION

This invention relates to quantitative assays for multiple analytes in a single fluid sample of biological origin. More particularly, the present invention relates to optical analytical methods based on rates of particle agglutination.

BACKGROUND OF THE INVENTION

Broadly applicable, accurate, sensitive and automatable assays are needed to monitor the presence and quantity of biological materials present in complex body fluids of patients at micromolar to picomolar concentrations in order to aid in diagnosis and therapy of disease.

Various methods utilized in the past, including liquid and gas chromatography, mass spectrometry, and numerous bioassay techniques, are time-consuming, costly and not readily automated.

Competitive protein binding assays such as radioreceptor assays and radioimmunoassays provided a major improvement in analytical sensitivity and productivity, but have the disadvantages of dealing with hazardous radioactive materials, and not being amenable to automation. While enzyme-linked and chemiluminescence-linked immunoassays and DNA probe assays have eliminated the hazardous radioactive materials, they have not solved the problem of a lack of automatability.

In recent years, a number of particle-based immunoassays have been developed to take advantage of the specificity of antibody reactions, while avoiding the complications of radiochemical labelling. Agglutination reactions involving bivalent antibodies and antigens or haptens of clinical interest have been utilized in both visual and quantitative assays with a wide variety of bacteria, red blood cells or polymer particles. Agglutination results from the growth of antibody (Ab)-antigen (Ag)-bridged particle aggregates to produce an extensive network that can be detected. Agglutination can result by adding the specific binding partner, either Ab or Ag, to the suspension of particles with immobilized Ab or Ag. At low concentrations of the specific binding partner, small aggregates consisting of only a few particles are produced. Particle-based diagnostic tests are usually based upon the very specific interaction of Ag and Ab. Ab or Ag can be adsorbed on submicron-sized polystyrene particles, often called "uniform latex particles". Bangs, L. B., *Uniform Latex Particles* Indianapolis: Seragen, 1984. These sensitized particles then act to amplify the visibility of the Ab-Ag reaction that takes place when a sample containing the sought Ag or Ab is mixed with these appropriately coated particles.

Suspensions of polymer microparticles in the colloidal size range of 0.02–100 $\mu$m diameter particles are available commercially. The properties of these particles are determined predominantly by the physicochemical properties of their surfaces. A single polystyrene latex particle is composed of a large number of individual polystyrene molecules (>1000 even for a particle as small as 0.1 $\mu$m diameter) held together by van der Waal's attractive forces. Each polymer molecule in the particle has end functional charge groups that are usually hydrophilic and that originate from a fragment of the compound used as the initiator of the polymerization. See, for a review, Seaman, G. V. F., "Physicochemical Properties of Latexes in Design of Latex Tests", in Seaman, G. V. F., ed., *Applying Latex Based Technology in Diagnostics*, Health & Science Commun., Washington, D.C., 1990, pp.1–19.

The usual form of polystyrene latex particles possesses sulfate charge groups for stabilization, but a variety of other functional groups can be introduced at the particle surface, such as hydroxyl, carboxyl, amine, and polymeric carboxylate groups. Such groups are particularly advantageous for binding to latex bead surfaces a wide variety of ligands and receptors.

Although, as noted above, sizes of polystyrene microspheres available commercially cover the range of 0.2 $\mu$m up to about 100 $\mu$m, the sizes used for serodiagnostic testing are predominantly in the range of 0.1 to 1.0 $\mu$m diameter. Performance characteristics are all influenced by particle size and monodispersity. Sedimentation under the force only of gravity may occur with the larger diameter microspheres, although this is not a major problem in the size ranges used in agglutination assays.

Uncoated latex particles form relatively stable hydrophobic suspensions because of like charge on all microspheres. When coated with a ligand such as Ag or Ab, the particles form stable hydrophilic suspensions remaining dispersed during storage, but aggregating when reacted with a complementary cross-reacting anti-ligand. The ligands used to coat latex particles are attached by one of three methods: (i) physical (passive) absorption; (ii) facilitated (forced) absorption; and (iii) covalent coupling.

Latex agglutination tests can employ either agglutination or inhibition of agglutination of particles. Conventional agglutination tests are used for the detection of Ab's or relatively high molecular weight Ag's, while agglutination inhibition tests are used principally for the detection of low molecular weight Ag's and also some larger Ag's.

When optical instruments that measure transmitted, absorbed or scattered light are used, it is possible to estimate agglutination of coated latex particles quantitatively and to develop sensitive particle immunoassays. The intensity of light scattered by particles dispersed in water varies with the number of particles, their diameter, the wavelength of the incident light, the angle of the detector to the incident light and several other variables.

As agglutination starts, single particles first become doublets; the number of monomeric light-scattering particles drops dramatically, and the apparent diameter of agglutinates increases rapidly. After this point, the changes in numbers and diameters are less rapid. An important aspect of particle agglutination, disclosed in the present invention below, is that scattered light intensity measured as a function of time can be the basis for a very sensitive kinetic immunoassay.

Several methods for quantifying particle immunoassays have already been devised. Instruments such as Coulter Counters® (Coulter Electronics, Hialeah, Fla.) that count numbers of particles or clumps of particles in discrete channels have been used to follow agglutination. As the particles of small size agglutinate, the signals disappear from one channel and appear in higher channels. One can thus count single particles as they decrease in number or count clumps of newly aggregated particles as they increase.

One can use a nephelometer to follow scattered light directly or a spectrophotometer to measure change of "absorbance" of light (measure scattered light indirectly). Angular anisotropy or dynamic light scattering or photon correlation spectroscopy are newer, even more powerful techniques for measuring particle agglutination quantitatively.

As noted above, traditionally, optical instruments such as turbidimeters or nephelometers that rely upon light scattering differences between agglutinated and unagglutinated particles have been applied to the problem of quantitating latex particle agglutination tests. Although such methods preserve the advantage of monitoring a homogeneous reaction mixture without the need for a separation step, they are satisfactory only for *single tests* and are not satisfactory for simultaneous, quantitative, multiple latex particle agglutination tests, which is the subject of the present invention below.

Light scatter from bulk solution of aggregating or dissociating immunobeads can be used to provide quantitative measurements of analyte concentrations. Turbidimeters measure light transmission through a suspension of particle aggregates, and nephelometers directly measure scattered light in specific directions. In both instances, light scatter from a mixed population of both aggregated and nonaggregated particles is measured. See, e.g., the LPIA ® nephelometer instrument of Mitsubishi Chemical Ind., Tokyo that is capable, however, of analyzing only one analyte at a time; Kapmeyer et al., U.S. Pat. No. 4,305,925 which discloses a nephelometric method wherein two different particle sizes are used to enhance the useful range of a latex agglutination immunoassay of a *single analyte*; and Ziege et al., WO 90/08961 who discloses a nephelometric quantitative immunoassay which employs coordinated carrier particles composed of copolymeric materials for the *detection* of a *single analyte*. There is no obvious way to extend the teachings of these patents to the use of a multiplicity of particle sizes to measure different analytes simultaneously.

It is well known that particles of different sizes, shapes and composition relative to the wavelength of light will scatter light differently in different directions. M. Kerker, *The Scattering of Light and Other Electromagnetic Radiation*, Academic Press, N.Y. 1969. It would be theoretically appealing to attempt to use the different angular scattering patterns of different particles in bulk solution in order to perform simultaneous assays. In practice, however, there is so much overlap in the angular scattering patterns of different particles that it becomes impossible to separate the results of one agglutination reaction from another.

As will be detailed below, the present invention employs an instrument for its simultaneous, quantitative multiple assay method that is neither turbidimetric nor nephelometric, but instead monitors light scattered from single particles or particle aggregates rather tan from many particles in bulk solution, and belongs to the class of instruments known as Flow Particle Analyzers (FPA).

Two types of FPAs have been used to detect particle aggregation by monitoring the size of individual particles or aggregates thereof as they flow individually through either an electronic or optical sensing zone. In the first type, particles and particle aggregates flow through a physically small, electronic sizing orifice, and in the second type the particles and aggregates flow through a focused optical beam. Although these approaches have been applied to quantitative latex particle agglutination assays (see below), neither has been successfully applied to the problem of simultaneous, quantitative multiple latex bead agglutination tests, and are limited to single tests or require complex signals to measure multiple analytes in a single sample.

Although electronic flow-through orifices can detect size differences among a population of electrically insulating particles, there are certain practical limits to using such devices in latex particle agglutination tests, due, in part, to the clogging of sensitive sizing orifices by high order aggregates unavoidably produced during agglutination tests and by particulate sample impurities. Masson, P. L. et al., *Methods in Enzymology*, 74:106 (1981); Cohen, R., U.S. Pat. No. 4,851,329. This limitation has prevented any routine, practical use of electronic sizing orifices in attempts to quantify latex particle agglutination tests.

As optical FPAs can use large bore capillary sensing chambers and, therefore, do not suffer from clogging as readily as do electronic devices, they are the preferred mode for single particle analysis approaches to quantitative latex particle agglutination assays, including immunoassays.

Optical FPAs that sense aggregate formation by the measurement of forward scattered light have been described by Masson et al. (ibid.), Masson et al. (U.S. Pat. No. 4,279,617), Cambiaso et al. (U.S. Pat. No. 4,184,849), and Cohen et al. (ibid.). Although these known systems are quantitative and sensitive, they disclose only single analyte assays, they are not aggregation rate-based methods, and they do not disclose simultaneous particle agglutination assays of multiple analytes in a single sample.

The Masson and Cambiaso systems, above, which sense forward scattered light pulses from non-aggregated particles that pass through a focused optical beam and which set electronic windows so as to ignore light pulses from aggregated particles, prefer the use of latex particles of two different sizes for agglutination, perhaps to lessen the effect that an initial distribution of multiplets (non-specifically formed without an Ag-Ab reaction occurring) may have on the assay reaction. Uzgiris et al., U.S. Pat. No. 4,191,739.

If particles of only one size are used, then the initial distribution of dimers, trimers and multimers must be taken into account when measuring the additional dimers, trimers, etc. that are created by the immunochemical process. On the other hand, if two differently sized particles are coated with the same immunochemicals needed to measure a given analyte, and are mixed together at the time the immunochemical reaction is run, then there will be no initial aggregates of the two sizes of particles. This may lessen the effect that an initial distribution of multiplets may have on the immunochemical reaction (see detailed description of the invention below).

While the use of different size particles are disclosed by Uzgiris et al., above, Masson et al., above, Cohen et al. above and Cambiaso et al., above, for single analyte testing by latex particle agglutination methods, none of these references disclose solutions to the problems of simultaneous multiple testing by latex particle agglutination. Indeed, the particle size recommendations made in these references are so incomplete that the inventions are unworkable even for single analytes. The present invention, as will be detailed below, is concerned with the specific means by which particles of differing sizes or refractive indices must be chosen and used in order to quantitatively monitor simultaneous multiple latex particle agglutination reactions.

Cambiaso et al., above, discloses a method for using a cross reactive antibody immobilized on one of the particle sizes and an antigen that reacts with only one of the antibody sites on the other size particle in an inhibition immunoassay. Although it is stated that the immobilized antigen gives specificity to the assay, and that, by choosing the correct immobilized antigen, an assay for that antigen in a patient sample can be carried out, this method specifically fails if one or more of the cross-reacting analytes is present simultaneously with other cross-reacting antigens. Therefore, the Cambiaso et al. system cannot be used for simultaneous multiple testing.

Abbott et al., U.S. Pat. No. 4,521,521, discloses a method for quantitatively measuring a *single analyte* in a liquid sample by measuring the rate of aggregation of analyte-bound particles. Measuring perpendicular light scatter is preferred. Abbott et al. do not teach a method of estimating multiple analytes simultaneously in the same sample, do not teach the use of different size or refractive index particles for each of multiple analytes in a single sample, and teach particles bound to analyte rather than to a ligand as in the present invention.

Abbott et al. above also disclose an analytical instrument for use with their immunoassay method. This instrument is, however, completely different in terms of concept, principle, design, electronics and operation than the optical flow particle analyzers of the present invention described below. Abbott relates to a particle size distribution measuring instrument, wherein count values for each particle size relating to the same analyte are obtained. Abbott et al. accomplish this, not by using single channel analyzers to separate pulse signals from a light detector into separate output signals or by using a peak detector means to sample peak height values of pulse signals from a detector and outputting corresponding peak height values, as are done in the instrument embodiments of the present invention, but, instead, by a counter network comprising a threshold comparator, a monostable multivibrator that generates a logic signal for each electrical pulse passing the comparator, and a counter in which is incremented the logic signals. The output of the threshold comparator equals the difference between the light detector pulse signal and a preset threshold level, and is not the output signal of the detector as is employed in the present invention. Further, the signals are representative of only a single analyte. The Abbott circuit does not separate the pulse signals from the detector, but merely triggers the comparator in an all-or-none fashion when a preset threshold level is exceeded. Because large multimers generate pulses of greater amplitude than do lower multimers or monomers, in the Abbott system the pulses from N-mer particles will exceed the thresholds of all channels and will increment all counters. These threshold circuits are clearly not single channel analyzers. Further, the threshold circuits of Abbott cannot sample peak height values, as is done by the peak detector means disclosed below, but rather are merely *triggered* when the signal exceeds a threshold. The signal may exceed the present threshold value, and trigger the circuit, before reaching its peak height value. In addition, the output of the threshold comparator is merely a pulse indicative of the fact that the pulse exceeded a threshold value; it provides no information as to the peak height of the signal, which peak height sampling is integral to the present FPA.

Cannon KK, JP 1207663, refers to a flow particle latex agglutination assay method and instrument for measuring multiple analytes simultaneously in a fluid sample. The patent employs particles coated with Ag or Ab specific for the Ab or Ag to be detected. Different particles may be of the same or different size. The method detects analytes by detecting light scatter in two directions, one of which is sideways, and uses an end point measurement of aggregation rather than a more advantageous rate-based assay as in the instant invention.

Thus, although particle agglutination-based assay methods that use flow or static particle analytical instruments are known, there remains an important need for a particle agglutination method capable of performing panels of in vitro laboratory tests, including immunoassays, on a simultaneous basis. That is, it would be greatly advantageous if such a simultaneous test could be performed by adding a single reagent combination to a single sample of a patient fluid sample without need to subdivide this sample, in contrast to present methods that require division of the patient sample, use of multiple reagents in multiple steps and collation of results at a later time. This need is now fulfilled by the invention described below.

SUMMARY OF THE INVENTION

The present invention comprises a novel quantitative, kinetic, particle agglutination method for simultaneously estimating the concentration of multiple analytes in an initial fluid sample that entails the use of a novel high resolution optical sheath flow cell, a single detector for measurement of pulse signals from unidirectional low angle forward light scatter from multiply-sized, differently-coated monomeric particles and their aggregated multimers, and a novel flow particle analyzer ("FPA") apparatus.

It is thus an object of this invention to disclose a method of performing analyses for multiple analytes in a single fluid sample, wherein measurement of a unidirectional low angle forward light scatter signature from monomeric and aggregated, multimeric polymeric particles as a function of time is correlated with analyte concentrations in the fluid sample, each analyte being measured using a particle of unique size or refractive index and unique coating.

It is a further object of this invention to disclose rate-based methods for the determination of aggregation of multiple-sized polymeric particles, each different size of particle being used to estimate the concentration of a different analyte in a liquid sample.

It is yet another object of this invention to disclose a method for determining an optimum range of particle diameters or refractive indices for use in the method of the invention.

It is still another object of this invention to describe simultaneous immunoassays of multiple analytes in a fluid sample using the particle aggregation rate method of the invention.

It is yet another object of this invention to provide sheath-type flow cell and flow particle analyzer embodiments specifically designed for the simultaneous multiple particle agglutination-based assay method of the invention.

These and other objects will become apparent to the reader by reference to the detailed description of the invention, the examples and the appended claims below.

DESCRIPTION OF THE DRAWINGS

FIG. 5A depicts the electronic layout of the flow particle analyzer of one embodiment of the invention.

FIGS. 5B-5E show an inset of pulse heights (B) and SCA Count Rate (C-E) for 3 populations of particles.

FIG. 7 shows the distribution of scattered light pulse heights obtained from two polystyrene spherical particle populations, with and without sheath flow.

FIGS. 14A-14D show FPA-generated histograms showing monomer, dimer and trimer populations after reaction of analyte IgA with polystyrene spheres of different monomeric sizes coated with anti-IgA antibody. Relative monomer diameters were 1.00 (A), 1.08 (B), 1.23 (C) and 1.46 (D).

DETAILED DESCRIPTION OF THE INVENTION

The present invention is a quantitative, kinetic, particle agglutination method for simultaneously measuring the concentrations of several analytes in a single fluid sample. The method entails the use of a novel high resolution optical flow particle analyzer instrument wherein detection by a single light detector of unidirectional low angle forward light scatter from differently sized and/or refractive indexed coated monomeric particles and their multimeric aggregates, is the basis of a stable kinetic method designed for simultaneous assays of multiple analytes in a single sample. The expressions "particles", "spheres", "microspheres" and "beads" are used interchangeably herein and are intended to refer to polymeric (e.g., latex, polystyrene) spherical particles of generally uniform diameter and refractive index relative to the surrounding medium.

Light Scatter

Single spherical particles scatter incident light according to the following parameters: (a) intensity of incident light; (b) diameter of the particle; (c) wavelength of the incident light; (d) refractive index of the particle; (e) refractive index of the surrounding medium; and (f) observation (scattering) angle. Theoretical analyses of light scattering from single spherical particles are available using these parameters. M. Kerker, 1969, above.

Light scattering from aggregates of spherical particles of different size (i.e., 2-mer, 3-mer ... n-mer) depends, not only upon the above parameters, but also upon the orientation of the aggregate in the optical beam and the specific configuration of the aggregate. For example, trimers can exist in a linear chain or in a triangular configuration. The enormous number of combinations of higher order aggregate configurations makes a practical computational analysis impossible. The description of the present invention relies, therefore, on a combination of theoretical and experimental observations.

Light scatter pulse heights or integrated pulse areas are not linearly related to the volume or any other simple measure of cluster size.

Figure 1:
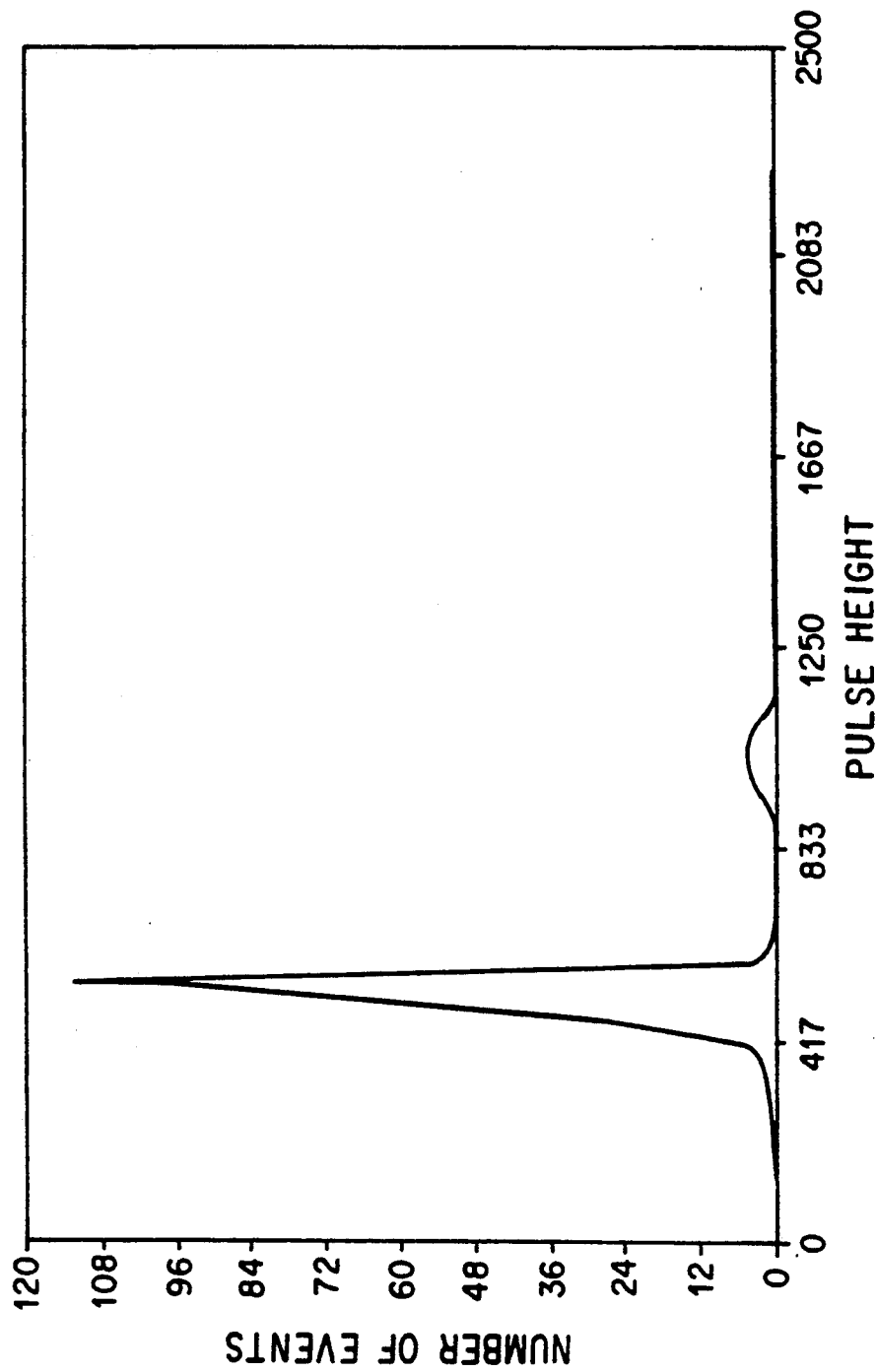
FIG. 1 shows flow particle analyzer-detected separations of monomers from dimers, trimers and higher multiplets.

Particles of a single size and shape can be resolved with high precision in an FPA. For "exact" spherical particles in the 1-10 μm range of diameters, it is common to have FPAs with 1.5% distribution widths of light scatter pulse heights. In other words, one can distinguish 1.00 μm particles from 1.01 μm particles (assuming that the digital electronics has a compatible resolving power). Thus, doublet (2-mer), triplet (3-mer) and higher multiplet (n-mer) distributions may be visualized electronically according to the invention with a FPA (FIG. 1). Although broadening of the multiplets may occur because of orientation effects, as the asymmetric clusters tend to be oriented by the sheath flow of the present method, this is minimal. The separation between multiplets becomes narrower as the size increases because of the nonlinear size correlation with pulse height.

The present invention uses spherical particles of different diameter or different refractive index for each analyte to be assayed, and relies on the ability of a flow particle analyzer to distinguish between particles and particle aggregates of different size or refractive index. Only the factors that affect size resolution in an optical flow particle analyzer limit the number of simultaneous assays that can be performed by this approach. Two of such factors, particle positioning effects and non-monotonic relationships between scatter pulse amplitude and particle size, and means to deal with those effects and relationships, are discussed below.

Size Resolution-Particle Positioning Effects

An optical flow particle analyzer provides a pulse of scattered light when each single particle or aggregate passes through the incident light beam. Optical beams cannot be made completely uniform in light intensity; therefore in order to achieve high size resolution, it is essential that particles and aggregates pass very nearly through the same region of the optical beam. This problem is not addressed in the latex particle agglutination flow particle analyzers described by Masson, P. L. et al., *Methods in Enzymology*, 74:106-139 (1981) and U.S. Pat. No. 4,279,617, Cambiaso et al, U.S. Pat. No. 4,184,849, or Cohen et al, U.S. Pat. No. 4,851,329. However, the present invention solves this problem by the use of "sheath flow".

In this sheath flow method, cells are centered in the flow by the use of a second, concentric stream that constricts the stream of cells to a narrow cross section and centers the cell stream in the highest intensity and most uniform region of the focused light beam. W. Gohde, et al., "DNA Measurements on Sperm and Blood Cells of Genetically Normal and Abnormal Humans" in *Flow Cytometry IV*, Universitetsforlaget, Bergen, Norway, 1980, pp. 273-276, and H. Shapiro, *Practical Flow Cytometry, Second Edition*, Alan R. Liss, Inc., New York, pp. 74.

Figure 2:
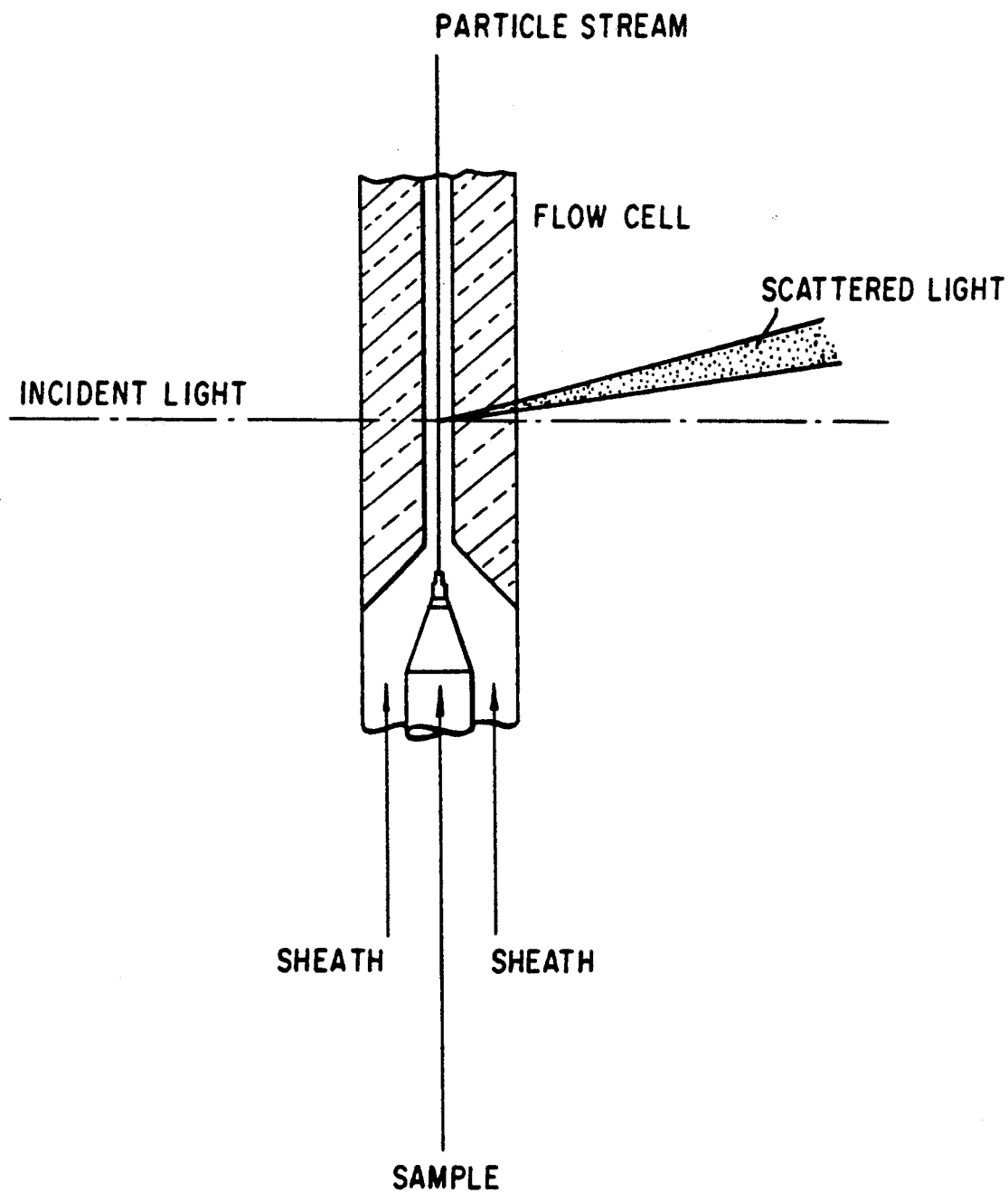
FIG. 2 is a sketch of the sheath flow cell of the flow particle analyzer of the invention.
Figure 3:
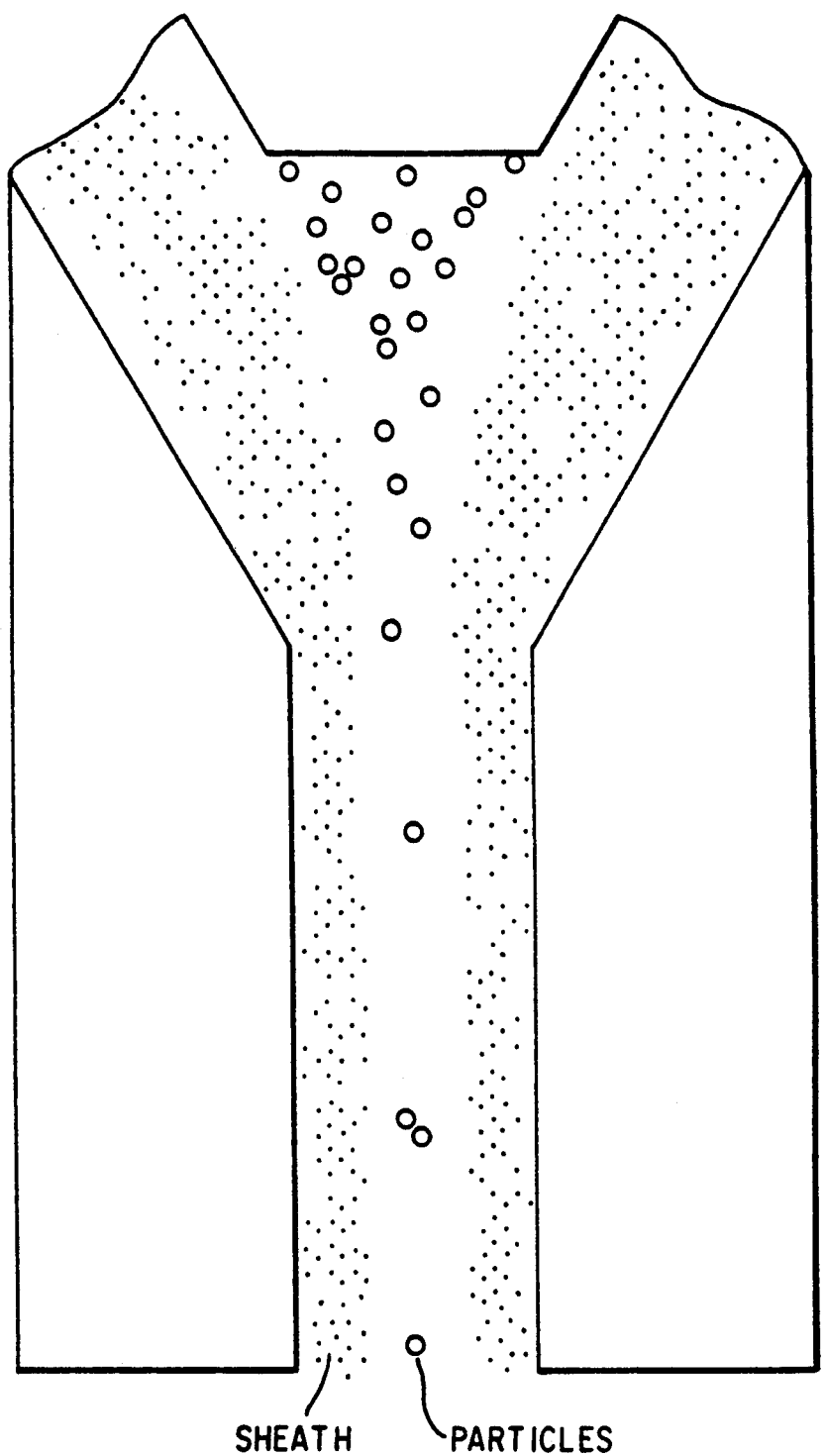
FIG. 3 illustrates sheath flow of particles through a flow cell.

The present invention uses sheath flow as a first step to obtaining maximum resolution in the light scatter signature of particles and particle aggregates. FIG. 2 is a sketch showing the essential components of the sheath flow cell of the optical flow particle analyzer of the invention. A sample is formed into a particle stream surrounded by sheath fluid in a flow cell. Incident light (e.g., narrow band laser beam) impinges on the particles at right angles, and scattered light is produced. FIG. 3 illustrates sheath flow in a downward direction.

Figure 4:
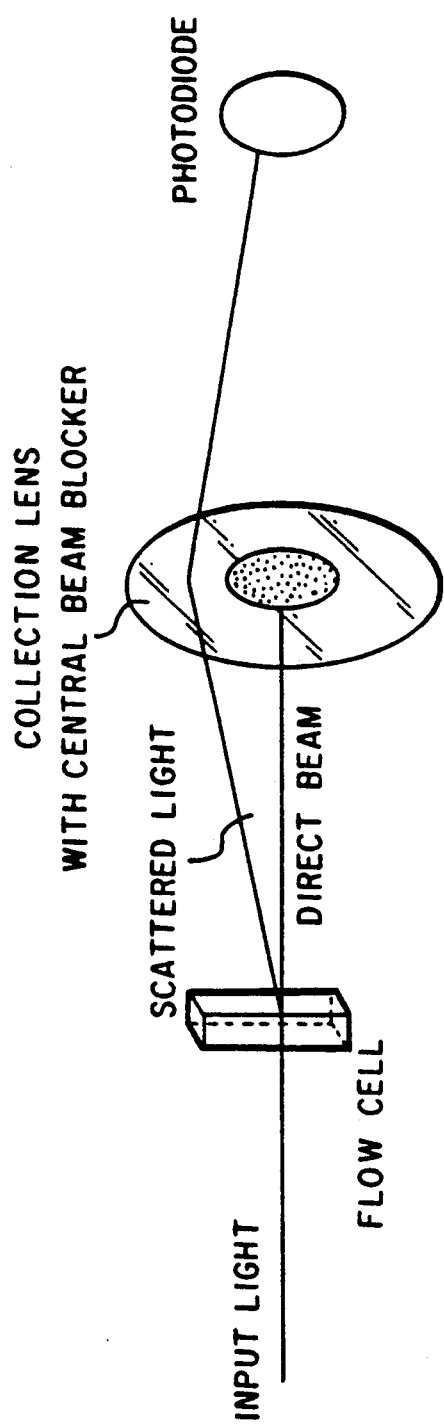
FIG. 4 shows the general layout of the optical system employed in the invention.

FIG. 4 is a sketch showing the general layout of the operatively-linked components of the optical system of the FPA used in this invention. The monomeric particle and particle aggregate-scattered light exiting from the sheath flow cell passes through a collection lens with central beam blocker, and impinges on a light detector. Suitable light detectors in accordance with this invention include photodiodes, photomultipliers, phototransistors and photoresistors. Each monomeric particle or particle aggregate that passes through the focal region of the optical beam produces a pulse of low angle forward scattered light that is received by a light detector.

Signals from the light detector may be analyzed in several ways; however, two advantageous embodiments of the present invention are preferred. The first embodiment is primarily a hardware-based method, whereas the second embodiment is primarily a software-based method.

In a first embodiment (FIG. 5A), pulses from the light detector are preamplified and monitored on an oscilloscope. Distinct populations of pulses with mean pulse height $V_M$ can be seen corresponding to each particle size and aggregate size (FIG. 5B). Single channel analyzers ("SCA")(Canberra Industries, Inc., Meriden, Conn.), one for each analyte, operatively linked to the preamplifier, are used to set electronic windows that pass a narrow range of pulse heights $\pm \Delta V$ around each distinct population mean pulse height $V_M$. Pulses that pass through each SCA are fed to separate inputs of an analog-to-digital converter ("ADC"), and then registered in a computer ("CPU"). The computer monitors the rate of arrival of pulses from each SCA, and presents this rate as a function of time. The count rate as a function of time for each of the three populations used in this example is shown in FIG. 5C. Various characteristics of the several count rate versus time graphs can be correlated with analyte concentration. These characteristics include initial rates of change, maximum rates of change, maximum count rates, relative dimer formation with time, differences in dimer:monomer count ratios with time, and time intervals (see Examples 2 and 4 below). Embodiments in which a separate preamplifier and an oscilloscope monitor are not used fall within the scope of this embodiment.

It should be emphasized that the use of three SCA units in FIG. 5 and in the accompanying description is merely one application of this embodiment of the invention. In other analytical applications, greater or fewer than three SCA units may be used depending on the number of analytes being simultaneously measured, as long as a different SCA is assigned to each unique coated monomeric particle corresponding to each analyte.

Figure 6A:
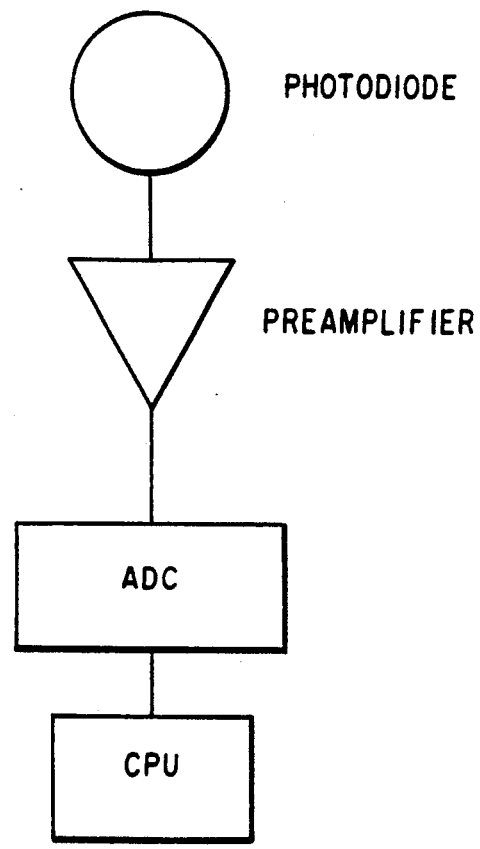
FIG. 6A shows the electronic layout of the flow particle analyzer of a second embodiment of the invention. Also shown in FIG. 6B as an inset is a plot of the total number of events versus pulse heights for two populations of particles.

In the second embodiment (FIG. 6A), the SCA components are disabled and all pulses are fed from a preamplifier directly to an ADC which samples the peak height of each pulse. The peak height values are then passed on to a computer, CPU. The computer sorts the peak height values by size and arranges then in a histogram.

The aforementioned histogram may be smoothed, if desired. This is done preferably by using a binomially-weighted moving average method. Those skilled in this art will know of other methods for smoothing histograms. In this preferred method, an interval of pulse height values along the "X" axis of the histogram is selected and binomial coefficients are used to weight the corresponding "Y" axis entries (number of pulses observed at each pulse height). For example, if an interval of seven pulse heights is elected, the seven entry row of Pascal's triangle (or table of binomial coefficients) is consulted and the number of pulses observed at each pulse height is multiplied by the corresponding entry in the Pascal triangle. These products are summed and divided by the sum of the seven Pascal triangle entries. The resulting value is entered as the new "number of pulse heights" at the middle pulse height. It is the nature of Pascal's triangle that this method gives the middle entry the greatest weight. The algorithm moves on by taking a new interval of pulse heights shifted by plus one on the "X" axis. The binomial weighting is then applied to the next "middle" data point. In order to achieve high rates of data analysis, this smoothing routine is applied to the entire histogram generally not more than twice. There is relatively little danger in applying this particular routine more than twice as the histogram does not become degraded through overapplication.

Figure 6B:
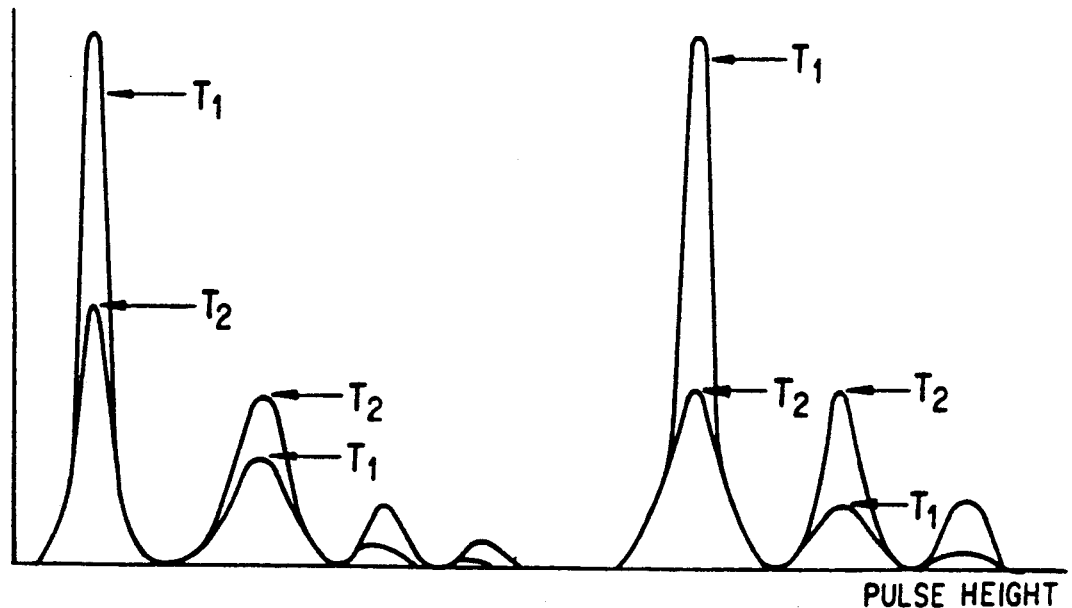

The peaks of the smoothed histogram are now easy to locate by a number of maximum value methods. A pulse height interval is selected bracketing each peak, and the total number of events are counted in that interval (equivalent to the area under the curve in FIG. 6B). This step takes the place of using SCA-determined windows as in the first embodiment (see FIG. 5). This "Total Number of Events" is divided by the adjustable time period described above to yield a "Count Rate" The count rate calculation is repeated at various times during the course of the particle agglutination reaction, with count rates plotted as a function of time, and the characteristics of these curves are used to determine the analyte concentration corresponding to each peak. As in the abovedescribed hardware embodiment, these characteristics may include initial slope, maximum slope, maximum count rate, relative dimer formation with time, differences in dimer:monomer count ratio with time, and time intervals.

FIG. 7 shows the distribution of scattered light pulse heights obtained from two polystyrene spherical particle populations with mean diameters of 1.6 $\mu$m and 2.03 $\mu$m, respectively. With sheath flow, the optical flow particle analyzer clearly distinguishes the two populations that have only a 0.43 $\mu$m difference in diameter. However, without sheath flow, the distributions overlapped, and were not readily distinguishable.

Sheath flow is useful in obtaining high resolution for fluorescence pulses in flow cytometry, regardless of the mass of fluorescent material in the particle. However, the analogous statement is not true for light scatter. I have determined that even with sheath flow, certain ranges of particle size are inherently non-resolvable. This result is not anticipated by prior art, and it is within the scope of the present invention to provide means for selecting those particle size ranges that can be used in conjunction with sheath flow to perform multiple assays.

Size Resolution—Non-monotonic relationship between light scatter pulse amplitude and particle size A complete optical wave analysis based on the theory of Mie (M. Kerker, 1969, above) shows that the scattered light pulse amplitude from spherical particles of uniform refractive index is not a simple monotonic function of particle diameter. This analysis shows that standing waves would be formed in spherical particles and would give rise to constructive interference for certain particle sizes (peaks in FIG. 8) and destructive interference for other particle sizes (valleys in FIG. 8). Constructive interference results in increased light scatter and destructive interference gives rise to decreased light scatter. The theoretical curve in FIG. 8 has been derived from an optical wave analysis. Theoretical analyses of light scattering are always approximate; however, the present experimental analysis (FIG. 10 below) clearly shows these constructive and destructive interference effects.

Figure 8:
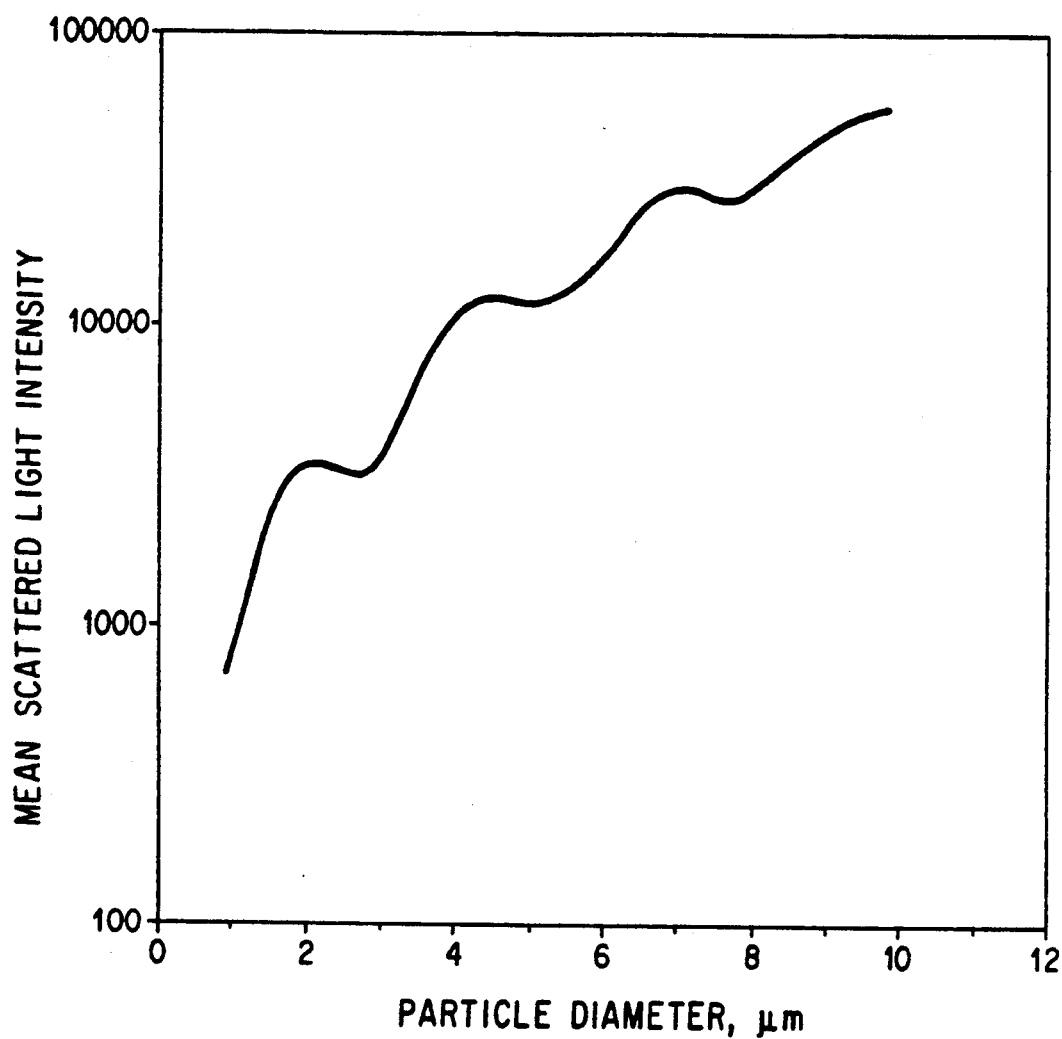
FIG. 8 shows a theoretical plot of mean scattered light intensity as a function of particle diameter. Data was taken from monomer peak channels.

Experimental data was obtained from a FPA and compared with the theoretical curve in FIG. 8. The FPA had the following characteristics. The light source was a helium neon laser operating at a wavelength of 632.8 nm and was focused to an astigmatic horizontal stripe with the approximate dimensions of 250 $\mu$m in the horizontal direction and 10 $\mu$m in the vertical direction. A sheath flow system was used to align the particles substantially in the central 10 $\mu$m of the beam focus. A lens was used to collect scattered light in a unidirectional low angle forward direction (between approximately 2 degrees and 7 degrees with respect to the optical axis of the system). Low angle forward scatter is highly advantageous. The present data show it to produce an approximately 100-fold better signal to noise ratio than right angle, i.e., perpendicular, scatter. Pulses of scattered light were detected by a photodiode, passed through an electronic preamplification stage, and then registered by pulse height in a data analysis system described above.

Figure 9:
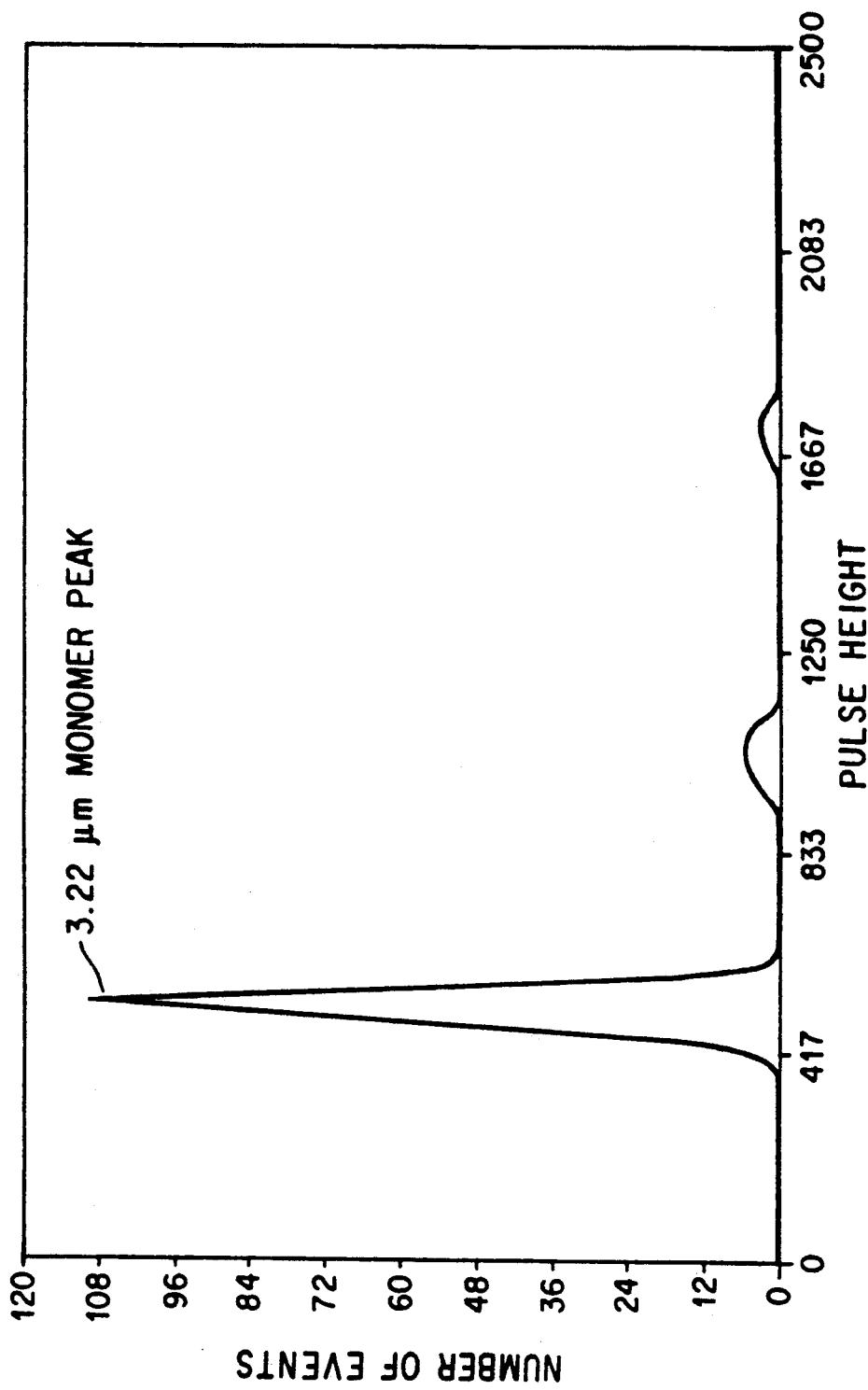
FIG. 9 shows the spectra of pulse heights obtained for uncoated 3.22 μm polystyrene latex particles.

Uncoated polystyrene latex particles (Polysciences, Inc., Warrenton, Pa.) were suspended in distilled water and passed through the FPA flow cell. Suspension in distilled water ensured that ion-induced aggregation of the uncoated particles did not occur. Spectra of pulse heights were obtained for each particle size and displayed for analysis as shown in FIG. 9. A plot of the mean pulse height versus particle diameter was made (FIG. 10), and can be compared to the theoretical curve (FIG. 8). Generally good agreement was obtained between theory and experiment; however, a systematic trend toward lower experimental pulse heights than had been predicted by the theory was noted for large particle sizes (right end of curve of FIG. 10).

From this curve, it can be seen that there are certain ranges of particle diameters that give light scatter pulses that are not resolvable even when sheath flow is used. For example, under the particular experimental conditions described in FIG. 10 above, particles with diameters in the 2 $\mu$m to 3 $\mu$m range (curve valley) were not resolvable from one another. This was also the case for particles with diameters in the range between 4.0 $\mu$m and 5.5 $\mu$m.

Figure 10:
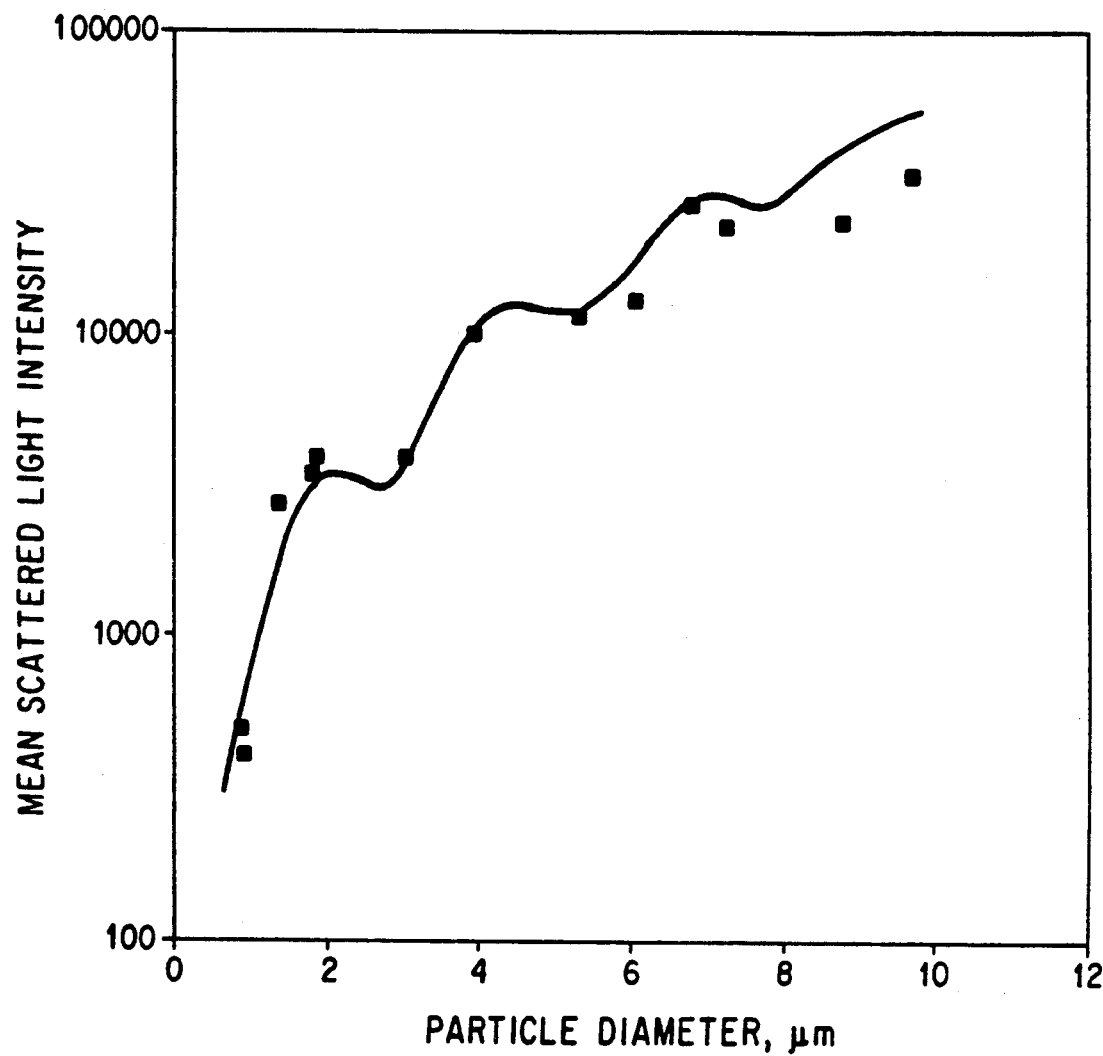
FIG. 10 shows a plot of the mean pulse height verses particle size, using the monomer peak channel data from the experiment shown in FIG. 9.

Generally, particles with diameters in the regions of steep slope in FIG. 10 are preferred for simultaneous assays because they are more readily resolved (see, e.g., FIG. 7). It is preferred to use particle diameters in the range of 0.02 to 12 $\mu$m. It is highly preferred to use particle diameters in the 0.5 to 7.0 $\mu$m range.

It is within the scope of this invention, and would not require undue experimentation, to use the method and FPA of the invention described above in order to select optically-resolvable particles for use in simultaneous assay of particular multiple analytes. Generally, the procedure involves suspending in an assay reagent solution appropriate to the particular analytes being estimated antibody-coated monomeric spheres of different diameter or refractive index. The assay procedure of the invention is then carried out with each unique sphere, using the optical FPA of the invention. After an appropriate reaction period, which typically begins at about three minutes after mixing of the reagents and continues to about 30 minutes, histograms are generated showing monomer, dimer and trimer populations as a function of voltage. By superimposing histograms (see, e.g., FIG. 14), optically resolvable sphere sizes are revealed by simple inspection.

Alternate to the above-described particle size selection method in which coated particles are used with an immunoassay reagent, uncoated particles may be suspended in a salt solution that causes slow dimer, trimer, n-mer formation (Reynolds, P. A., et al., Colloids and Surfaces, 23:273-299 (1987)). For example, polystyrene spheres may be suspended in 0.35M NaCl and stirred for ten minutes; samples drawn periodically are then analyzed by the optical FPA system of the invention, and histograms developed.

The curve for light scattering pulse amplitude versus particle diameter is altered when changes are made in the refractive index of the particles, the refractive index of the suspending fluid, the wavelength of the incident light, or the angle of observation for scattered light. Optimal particle diameters for simultaneous assays must be determined as shown above for any given combination of the above parameters. The present invention utilizes particles chosen from these optimal regions in order to maximize the number of simultaneous assays that can be performed.

Any chemical reaction that can couple two beads can be monitored by the method of the invention. For example, multiple antigen-antibody reactions, wherein antibodies are the analytes in the patient sample being assayed, may be assayed simultaneously on the same patient fluid sample by using beads of different diameters, each with a different antigen coating containing an epitope to the antibody. Similarly, beads may be coated with an antibody directed against an epitope of an antigen analyte.

The method of the invention is flexible. It may be used to measure either agglutination or inhibition of agglutination of coated particle. Components of the reaction mixture may be added concurrently or sequentially. The method may also be applied to competition or sandwich systems wherein differently coated particles compete for binding to an analyte ligand in a competition assay.

It is within the scope of the method of the invention to detect bead aggregation in blood or plasma that is undergoing a clotting reaction. Such reactions are useful in measurements of hemostasis.

The ability to carry out multiple analyte assays, clotting assays and cell counts simultaneously and on the same instrument is a major advantage over current practice that would use three different instruments for this purpose. The method and FPA of the invention are ideal for exploiting this kind of combination testing.

The following examples are presented merely to provide specific embodiments of this invention, and are not intended to provide any limitations to the invention not set forth in the claims.

EXAMPLE 1

Simultaneous Independent Immunoassays for Two Analytes

A simultaneous immunoassay for human IgG and human IgA was performed using the sheath flow optical FPA system shown above.

Two sizes of Polystyrene Microspheres ® (Polysciences, Inc., Warrington, Pa. 18976-2590) were each suspended to 0.5% (w/v) in 20 mM HEPES buffer, pH 8.0. The 1.23 $\mu$m beads (coefficient of variation of diameter of particles ranged from 0.1% to 4.0%) were incubated with 22.5 $\mu$g/mL rabbit anti-human IgA antibody and the 2.05 $\mu$m beads were incubated with 17.5 $\mu$g/mL rabbit anti-human IgG antibody (Jackson Immunoresearch Laboratories, Inc., West Grove, Pa.) for 30 minutes. The antibody coated beads were then coated with 0.2% nonfat dry milk solids (Carnation Company, Los Angeles, Calif.) for 15 minutes in order to block nonspecific binding sites. Coated beads were washed by repeated suspension in storage buffer (1.5M NaCl containing 0.5% bovine serum albumin and 0.1% NaN$_3$, pH 7.4), and centrifugation. Control beads were coated with nonfat dry milk solids for 15 minutes and washed as above.

Electronic windows were set to monitor the count rate of monomers of these two bead sizes as they passed through the sensing zone of the analyzer. The initial time rate of change (negative slope) of the instantaneous count rate of monomers was measured and quantitatively related to the concentration of analyte. A data analysis method was used that ignored the initial lag phase of the reaction which usually ranges between 3 and 3.5 minutes after mixing. During this agglutination lag phase, analyte diffuses rapidly to the beads but very few collisions have yet occurred between beads, and detectable agglutination has not yet occurred. After the lag phase, the less mobile beads collide and agglutinate at a rate that depends on the analyte concentration.

Figure 11:
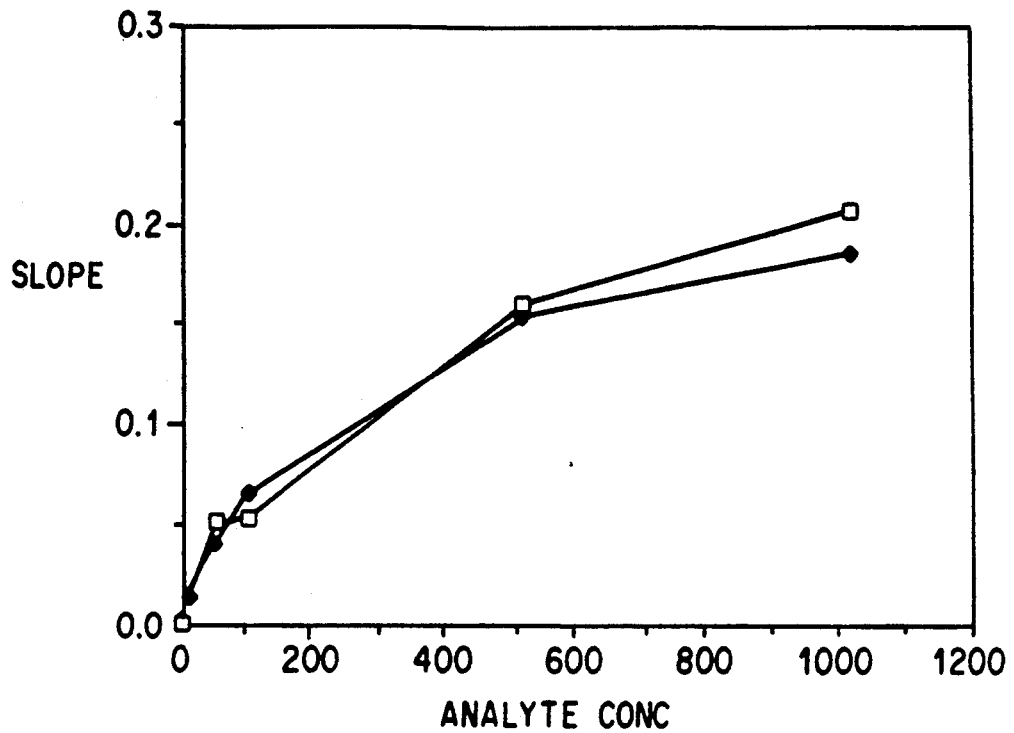
FIG. 11 shows the results of the kinetic assay method of the invention applied to immunoglobulin IgA in the presence of IgG ( ), compared to IgA analyzed alone ( ).

The results of these experiments are summarized in FIGS. 11 (IgA alone and simultaneously with IgG) and 12 (IgG alone and simultaneously with IgA). These curves show the initial rate of monomer decrease versus analyte concentration for the two analytes alone and then together. There was no significant difference between the data taken when the analytes were measured alone or simultaneously. It is concluded that the reactions remained independent of each other even when the two immunochemical reactions occurred in the same reaction mixture.

Figure 14C:
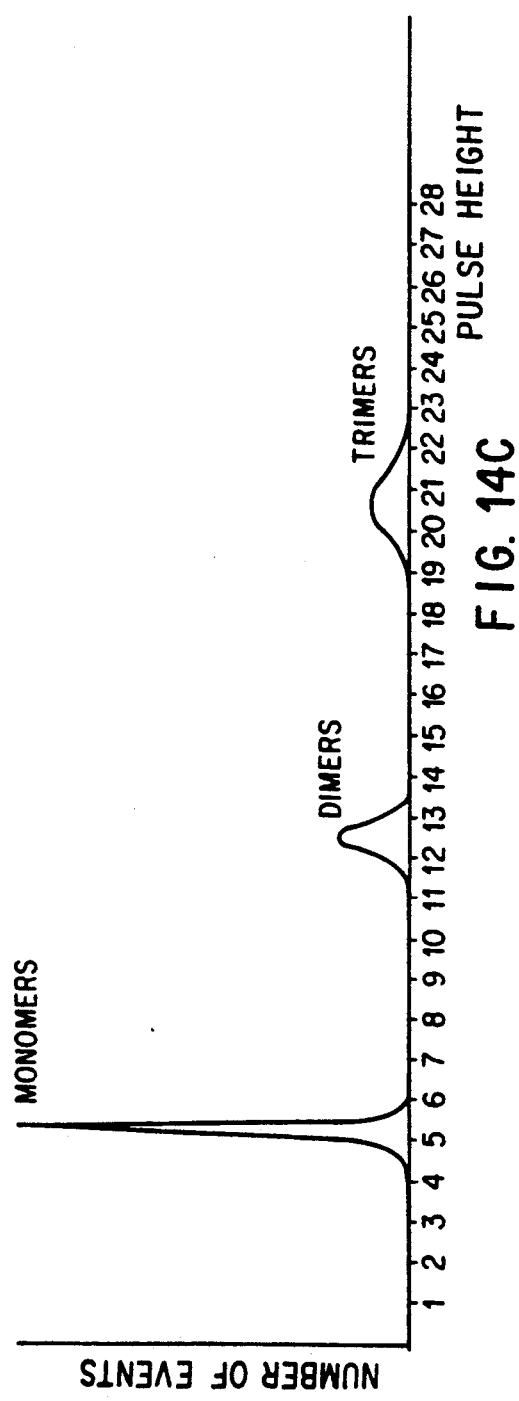
Figure 14D:
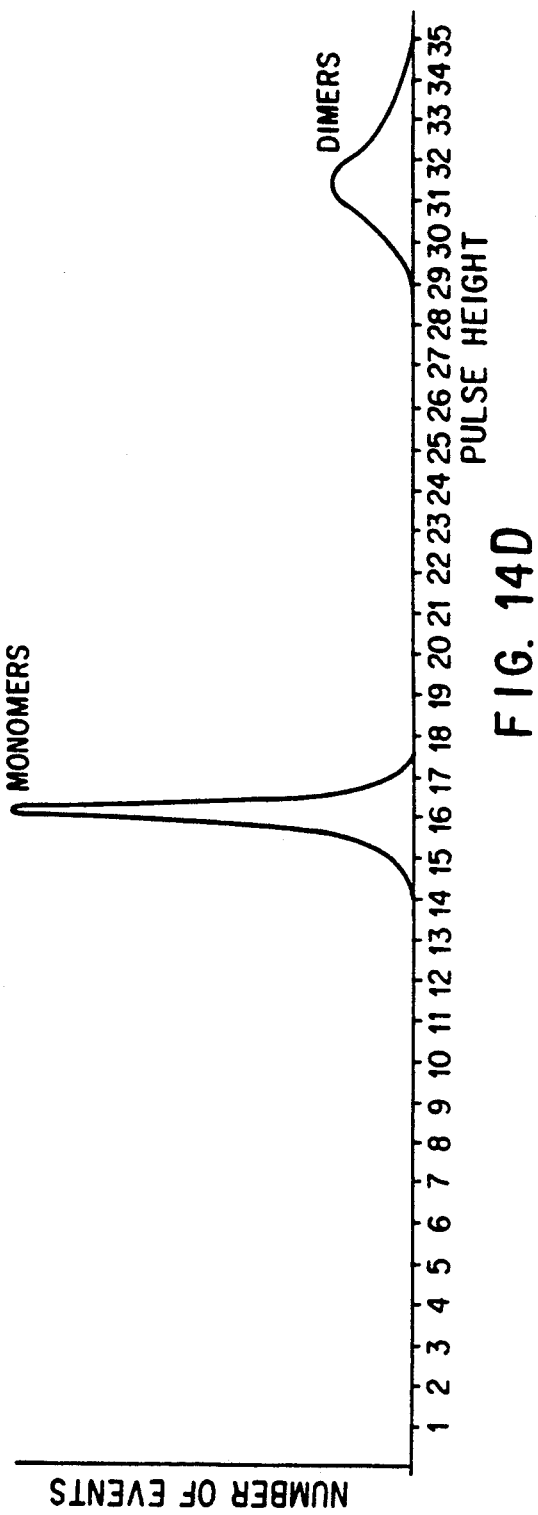

This independence can be traced directly to the use of sheath flow and the use of different sized beads taken from the appropriate regions of the light scatter versus bead diameter curve (FIG. 10) or from the superimposed histograms of FIG. 14.

EXAMPLE 2

Kinetics of Dimer Formation in an Assay of Thyroid Stimulation Hormone in Human Serum An immunoassay for human thyroid stimulating hormone (TSH) in human serum was performed using the sheath flow optical FPA system described above.

Polystyrene spheres (Interfacial Dynamics Corp., Seattle, Wash.) of 1.62 $\mu$m diameter were coated with anti-TSH monoclonal antibodies by incubating the spheres overnight in a solution of 100 mg/mL of antibody in 10 mM HEPES buffer, pH 7.5. Coated spheres were recovered by brief centrifugation, and washed three times in a 4-fold volume of 10 mM HEPES buffer, pH 7.5, containing 0.1% (w/v) BSA and 0.01% NaN$_3$.

Coated spheres were then suspended in 20 mM glycine buffer, pH 9.3, containing 0.1% BSA, 0.01% NaN$_3$ and 300 mM NaI. This reagent was added to an equal volume of standard human serum (OEM Concepts, Inc., Toms River, N.J.) containing known concentrations of human TSH, and continuously stirred. The initial concentration of monomeric spheres was about $5 \times 10^7$ monomers/mL. Dimeric spheres, present as a result of the manufacturing and coating processes, were about 2% of the initial monomer concentration. The concentrations of TSH in the reaction mixture were 0.0 $\mu$IU/mL (control, ○ in FIG. 13), 1.0 $\mu$IU/mL ( in FIG. 13), 25 $\mu$IU/mL ( in FIG. 13), or 100 $\mu$IU/mL (□ in FIG. 13).

Reaction mixtures were sampled at intervals over the course of 15 minutes from initiation of the reaction, and analyzed by an optical FPA system of the invention. Dimer count rates were measured either as raw count rates from the dimer windows, or relative count rates obtained as a ratio of dimer to monomer count rates or dimer to hardware control bead (no analyte) count rate. The relative dimer count rates ("Relative Dimers") for four different TSH concentrations are shown in FIG. 13.

Each analyte reaction curve (Relative Dimers v. Time) shows an initial lag phase with a low slope. Each curve also shows a phase in which the slope is maximal, following the lag phase. The time required to reach a maximum slope decreases with increasing analyte concentration. The maximum slopes clearly increase with increasing TSH concentration. The maximum percent dimers (or relative dimers) compared to the monomers is greater with increasing analyte concentration, and the time necessary to reach this maximum increases with decreasing analyte concentration. In addition, the area under each curve increases with increasing TSH concentration when integrated over the same time limits. It is important to note that, although all of the aforementioned characteristics of the reaction curves are related to TSH concentration, none is necessarily linearly related.

The count rate plots versus time illustrate characteristics that cannot accurately be predicted by mathematical models. The nonmonotonic behavior of the curves, especially at high analyte concentrations, is surprising and must be considered on an analyte-by-analyte basis. For example, the time at which a TSH reaction reaches a maximum dimer count rate is different than the time necessary for an IgE assay reaction (cf., Example 1) to reach its maximum dimer rate, even if the molar concentrations of the analytes are the same. These differences must be taken into account in calculating the most useful plot characteristics that are related to analyte concentration.

Figure 13:
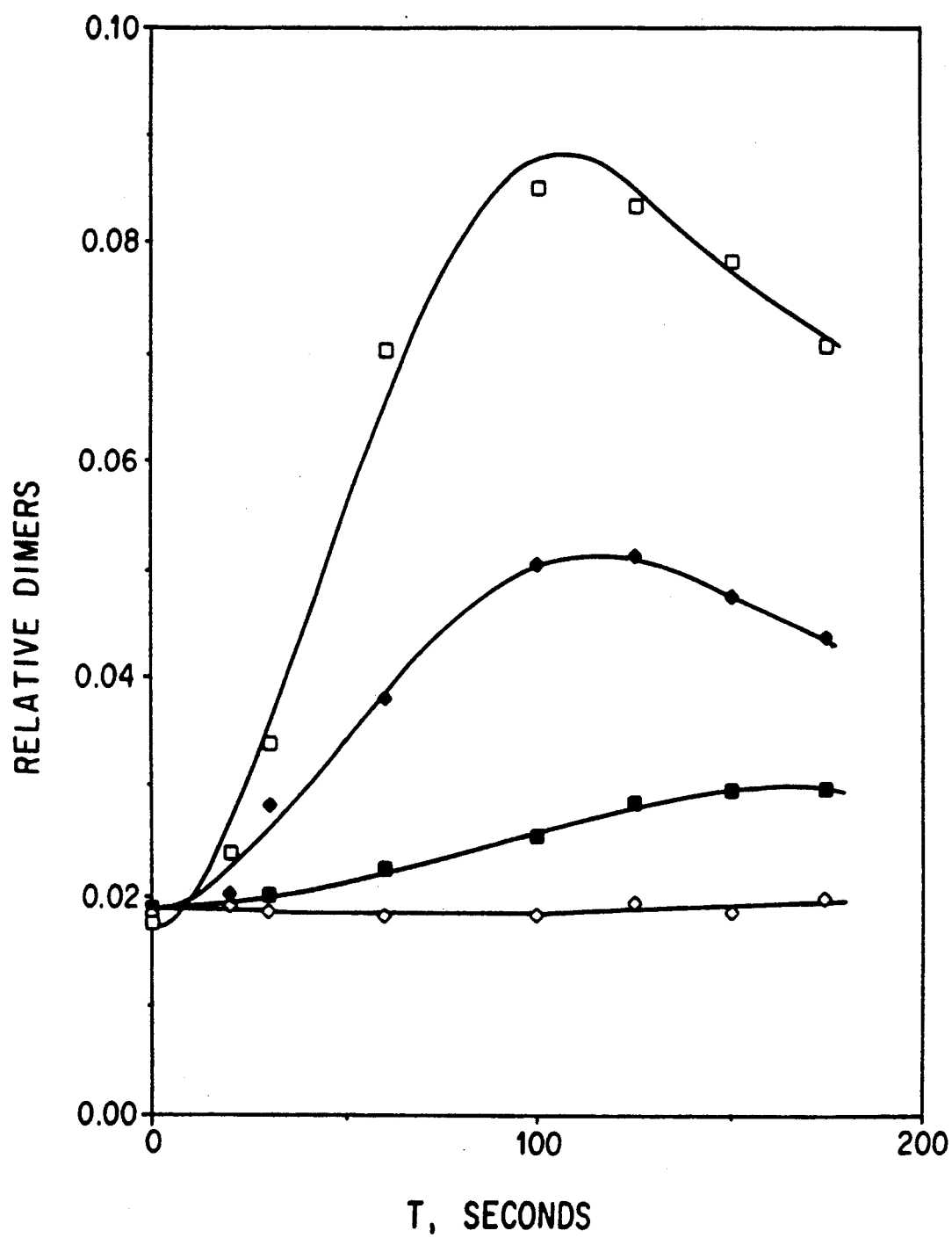
FIG. 13 shows relative dimer formation as a function of time during the application of the kinetic assay method and the sheath flow optical FPA system of the invention to the immunoassay of human thyroid stimulating hormone (TSH) in human serum, at concentrations of TSH (in μIU/mL) of 0.0 (○), 1.0 ( ), 25 ( ), and 100 (□).

The plot characteristics shown in FIG. 13 were not altered significantly when absolute or relative dimer count rates were obtained by: 1) sending pulses from an SCA set to accept dimer pulse heights to an ADC and then to a CPU; 2) sending pulses from an SCA set to accept monomer count rate where the dimer count rate originated from a separate SCA, and combining these by CPU to form a ratio of dimer to monomer count rate; or 3) sending pulses from an SCA set to accept monomer pulse heights from 1.05 μm hardware control particles to an ADC, and forming the ratio of dimer to hardware control particles count rates where, again, the dimer count rate originated from a separate SCA.

Similar reaction curves were produced when a peak detector analyzer means was used with an ADC to form histograms of pulse heights via a CPU (software embodiment). In this embodiment, a CPU was used rather than SCAs to bracket windows for the monomer and dimer populations, whether smoothed or unsmoothed histograms were used. Repeated samplings of the reaction mixtures over 15 minutes produced reaction plots that were not different than those shown in FIG. 13.

Precision in these experiments was affected by the number of particles of each monomer counted, and by the stability of the FPA fluid flow rate when ratios of reacting dimers to reacting monomers or ratios of reacting dimers to hardware control beads were not used.

EXAMPLE 3

Determination of Optical Resolvability of Coated Polystyrene Spheres

Four sizes of polystyrene spheres (referred to hereinafter as A, B, C and D) (Polysciences, Inc.) were coated with anti-IgA antibody as in Example 1. Coated spheres were washed and nonspecific binding sites blocked as described in Example 1.

Suspensions of each size of coated spheres were then reacted, separately, with a fixed concentration of IgA (1 mg/mL) for 15 minutes, using the kinetic method and FPA of the invention as described above. The relative monomeric diameters of the sphere prior to reaction with analyte stood in the ratio of 1.00 (A), 1.08 (B), 1.23 (C) and 1.46 (D). Histograms showing monomer, dimer and trimer populations were generated with the optical FPA.

Referring to FIG. 14, superimposition of the four sets of curves reveals that spheres A and B, spheres A and D and spheres C and D are optically resolvable, as the early reaction histogram yielded peaks that were clearly distinguishable from each other. In contrast, spheres B and C, and spheres A and C are not optically resolvable because of overlapping monomer and dimer peaks. According to this analysis, then, combinations of spheres A and B, spheres A and D, and spheres C and D could clearly be employed in a simultaneous assay of two analytes.

EXAMPLE 4

Simultaneous Assay of TSH, IgE and IgA in a Single Sample

A simultaneous multiple immunoassay was performed on three analytes—human TSH, IgE and IgA using the sheath flow optical FPA system described above.

Figure 15:
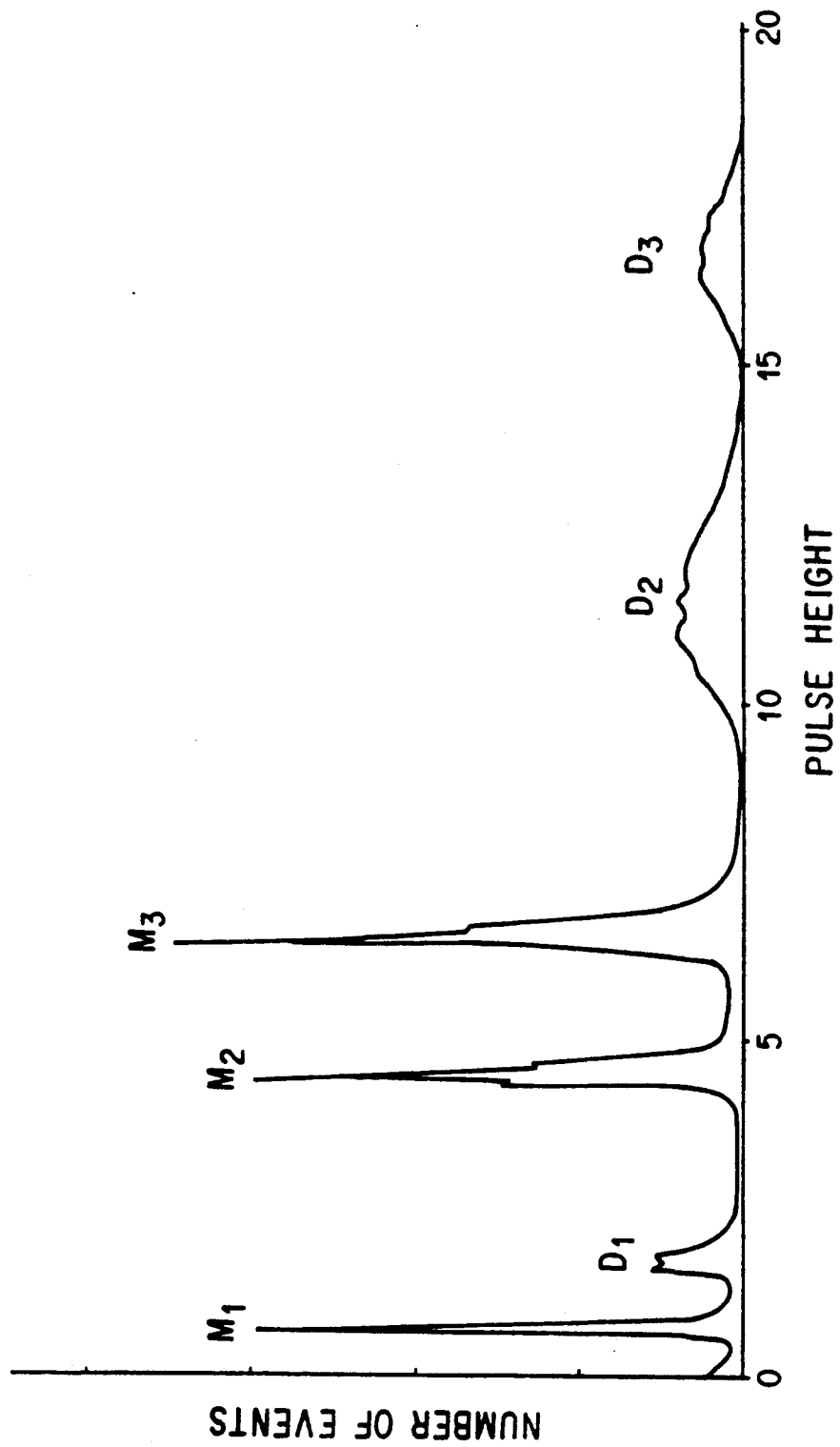
FIG. 15 shows a pulse height histogram showing the optical resolvability of monomers and dimers of three sizes of polystyrene microspheres. In the figure, $M_1$ and $D_1$ represent monomers and dimers of 1.05 μm spheres, $M_2$ and $D_2$ for 1.62 μm spheres, and $M_3$ and $D_3$ for 1.78 μm spheres.

Polystyrene spheres (Interfacial Dynamics) of diameter 1.05 μm, 1.62 μm and 1.78 μm were selected as being optically resolvable using the criteria of Example 3. In this selection process, uncoated microspheres were induced to aggregate slowly by stirring the particles in the presence of 0.35M NaCl for ten minutes. The suspension was then analyzed by the sheath flow optical FPA system, and histograms were developed. The pulse height histogram is shown in FIG. 15. $M_1$, $M_2$ and $M_3$ in the figure represent the three monomeric species, and $D_1$, $D_2$ and $D_3$ the three dimeric species, of the 1.05 μm, 1.62 μm and 1.78 μm spheres, respectively.

Spheres were coated with antibodies as described in Examples 1 and 2. The 1.05 μm spheres were coated with anti-human TSH antibodies, the 1.62 μm spheres with anti-IgE antibodies, and the 1.78 μm spheres with anti-IgA antibodies.

Human serum, stripped of TSH, IgE and IgA content (OEM Concepts, Inc.) was used as the vehicle for analytes TSH, IgE and IgA, which were added to this serum in known concentrations (see Table 1).

The reaction solution was the same as described in Example 2. The aforementioned serum standard solutions represented 10% (v/v) of the total reacting mixture.

The initial monomer concentration was $5 \times 10^7$/mL for each sphere size. Initial dimer concentrations were approximately 1.5% in each case.

All reaction mixtures were sampled by the FPA system over a period of about 20 minutes. Stirring of reaction mixtures is necessary for particle aggregation to occur. Therefore, reactions did not continue in aliquots removed from the reaction mixture for FPA analysis.

Figure 16:
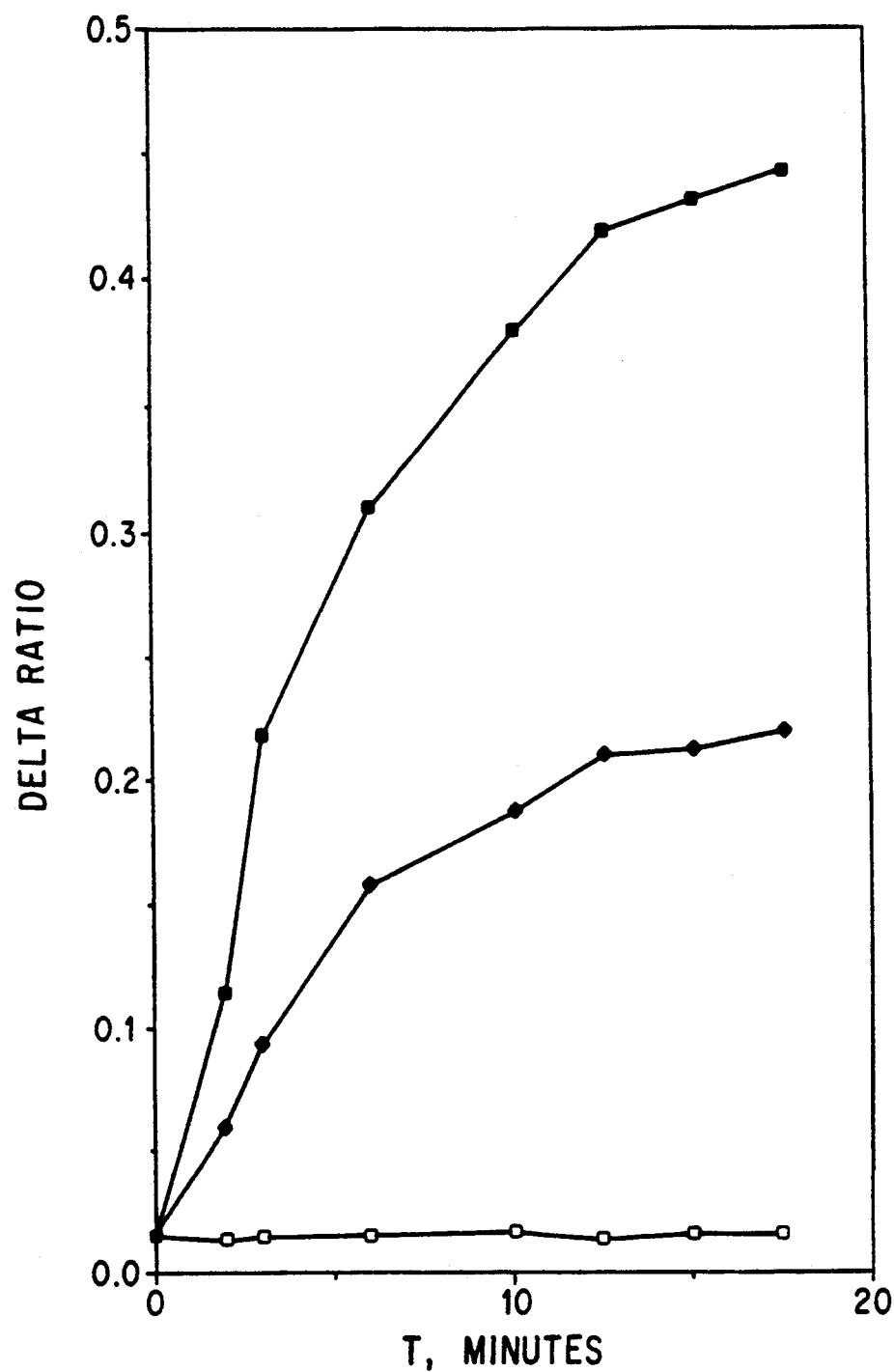
FIG. 16 shows the kinetic curves generated by simultaneous multiple analyses of IgA, IgE and TSH using the optical FPA of the invention. Ratios of dimer to monomer are plotted as a function of time. Actual analyte concentrations for each curve are listed in Table 1 of Example 4. In the experiment, there is a "zero" IgA control.

In FIGS. 16 (Response to IgA), 17 (Response to TSH) and 18 (Response to IgE), TSH is expressed as μIU/mL, IgE is in IU/mL and IgA is in mg, μg or ng/mL. Actual concentrations in each experiment are shown in Table 1.

TABLE 1

| FIG. | Curve Symbol | IgA | TSH μIU/mL | IgE IU/mL |
|---|---|---|---|---|
| 16 | □ | 0 | 2 | 100 |
|  |  | 500 ng/mL | 1 | 25 |
|  |  | 1 μg/mL | 2 | 100 |
| 17 | □ | 1 μg/mL | 2 | 100 |
|  |  | 500 ng/mL | 1 | 25 |
|  |  | 5 mg/mL | 0 | 100 |
| 18 | □ | 1 μg/mL | 2 | 100 |
|  |  | 500 ng/mL | 1 | 25 |
|  |  | 5 mg/mL | 2 | 0 |

Figure 17:
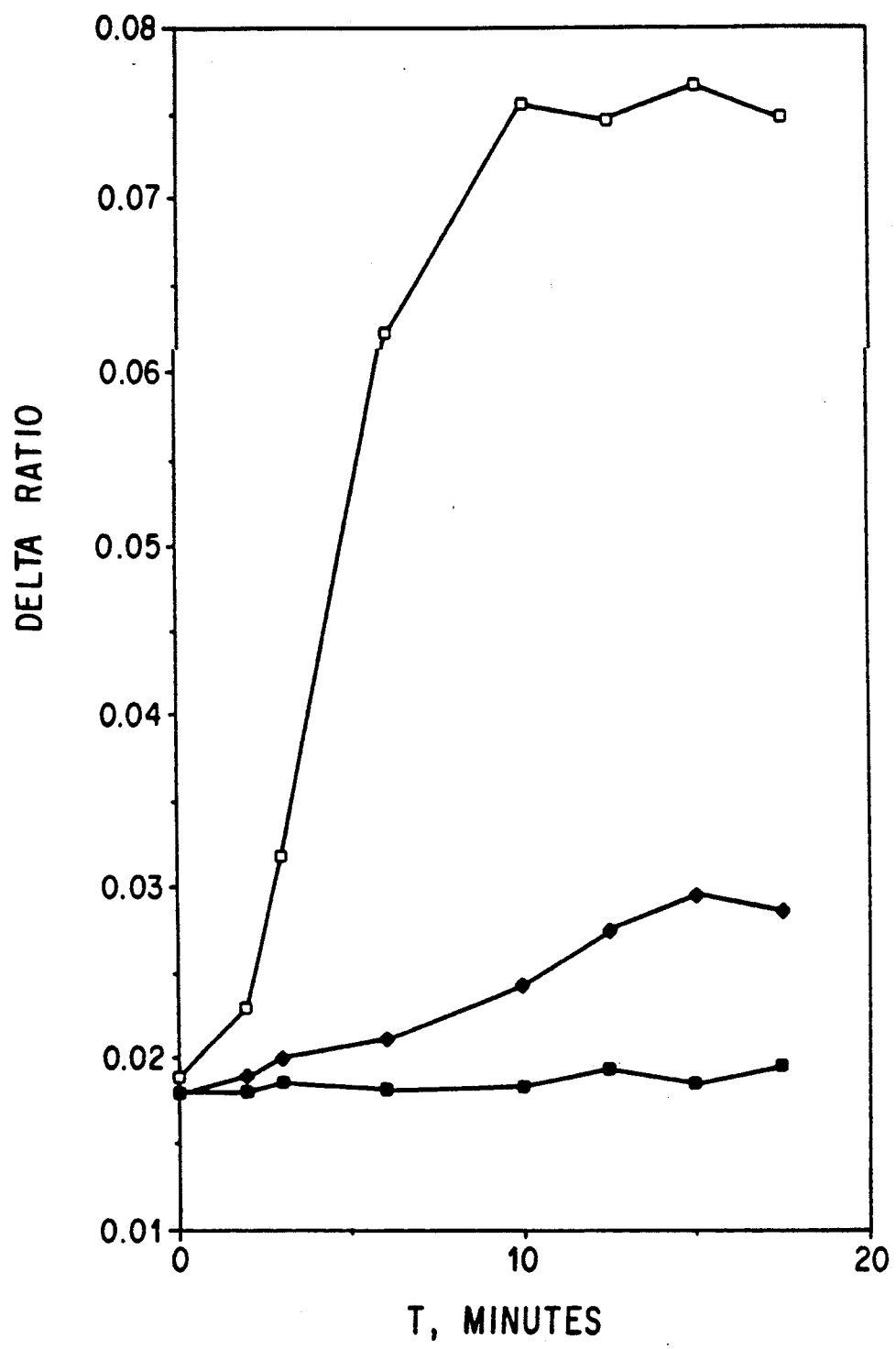
FIG. 17 is the same as in FIG. 16, except that there is a "zero" TSH control.
Figure 18:
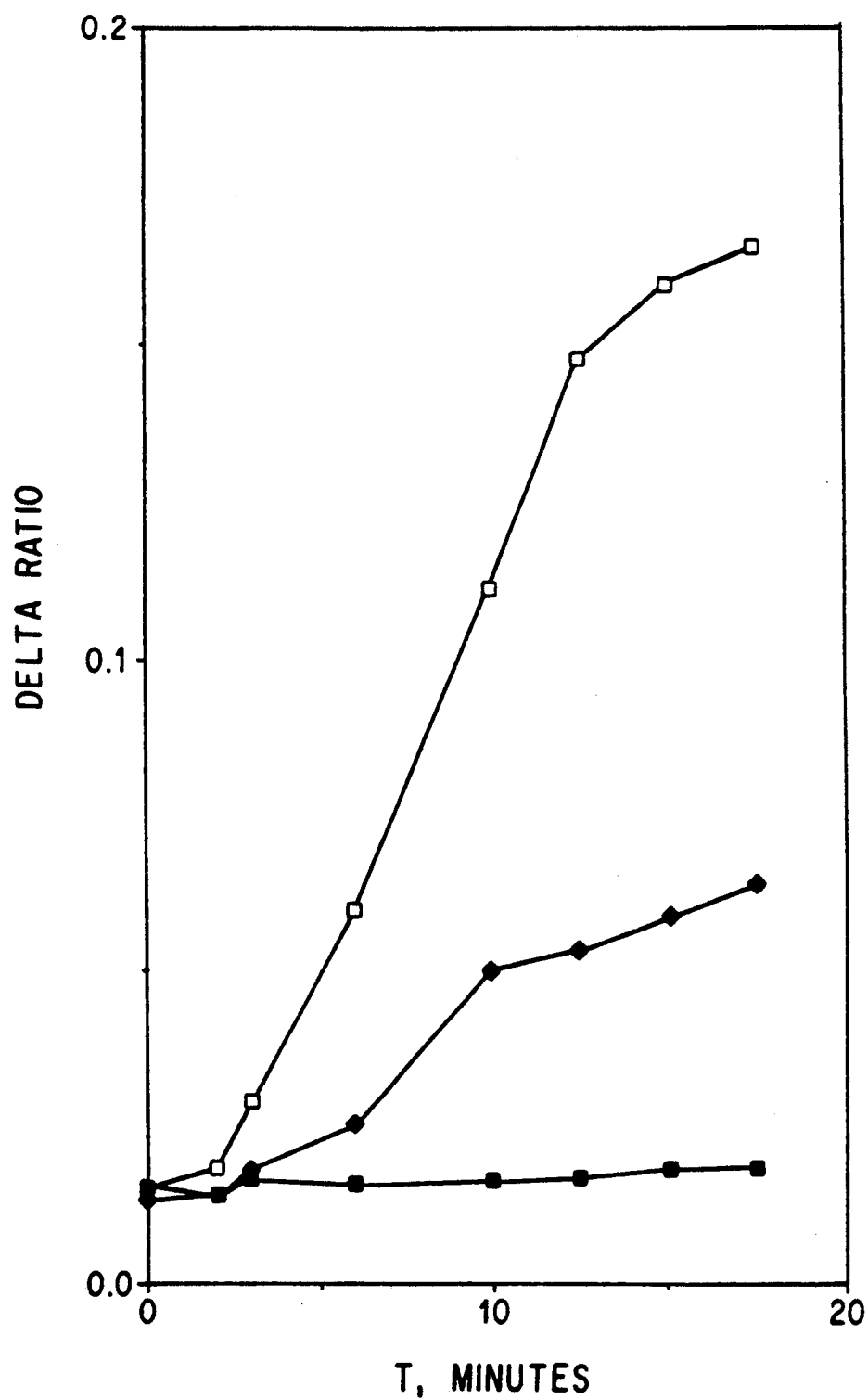
FIG. 18 is the same as in FIG. 16, except that there is an IgE "zero" control.

The standard kinetic curves of FIGS. 16–18 were generated by plotting the changes in dimer:monomer ratio ("DELTA R") with time for each set of analyte concentrations.

Each reaction kinetic curve was clearly separable, and showed no detectable "cross-talk." This was established as follows. Each "zero" analyte concentration was read in the presence of a high concentration of the other two analytes. In FIG. 16, IgA is seen as being "zero", in FIG. 17, TSH was "zero", and in FIG. 18, IgE was "zero" (see Table 1 for details). As the "zero" curves showed no discernable slope, it can be concluded that neither of the other two analytes, even at high concentration, produced inter-assay interaction. At the extreme, when IgA was present at over $10^{-5}$M (5 mg/mL), the apparent TSH zero value in FIG. 17 ( ) was no greater than about $10^{-12}$M, i.e., seven orders of magnitude lower than was the actual analyte concentration. Such a rejection ratio is sufficient, even for the most extreme requirements in a clinical setting.

As described in detail above, various plot characteristics in FIGS. 16–18 may be correlated with analyte concentrations in order to make this experiment the basis of the simultaneous quantitative estimation of TSH, IgA and IgE in a single fluid sample.

I claim:

1. An optical flow particle analyzer for simultaneous assay of multiple analytes in a single fluid sample by a rate-based particle aggregating method, comprising:
   a) a light source;
   b) an optically-defined viewing zone upon which viewing zone focused light from said light source is incident;
   c) means for flowing through said viewing zone a reaction mixture comprising said single fluid sample and a reagent comprising, for each of said multiple analytes, monomeric coated particles of a diameter or refractive index unique for each said analyte, such that each said particle of unique diameter or refractive index or aggregate thereof produces a pulse signal from unidirectional low angle forward light scatter that is distinguishable optically from a pulse signal from unidirectional low angle forward light scatter produced by any other monomeric coated particle of unique diameter or refractive index or aggregate thereof wherein each said unique coated particle is coated with a unique composition that corresponds and binds specifically to a corresponding analyte so as to form aggregating coated particle-analyte binding pairs, so that unique monomeric coated particles or aggregated multimers formed therefrom flowing through said viewing zone produce discrete pulses of scattered light unique for each said unique coated particle-analyte binding pair or aggregated multimer thereof;
   d) lens means for collecting said pulses of unidirectional low angle forward scattered light;
   e) single light detector means for receiving collected pulses of said unidirectional low angle forward scattered light and converting said collected pulses into electrical pulse signals, each of said pulse signals being unique for each said coated particle monomer or each said aggregated multimer corresponding to different analytes;
   f) analyzer means for separating said electrical pulse signals into separate output signals, each of said separate output signals representative of a different analyte, wherein said analyzer means comprises a plurality of single channel analyzers, each of said single channel analyzers being dedicated to each said coated particle monomer of unique diameter or refractive index, or aggregated multimer thereof, each of said unique monomers or multimers thereof corresponding to each of said multiple analytes, such that each of said single channel analyzers monitors the pulse signals from each of said coated monomeric particles of unique diameter or refractive index, or aggregated multimers thereof, and such that each said dedicated single channel analyzer passes as output signals, signals falling within predetermined ranges of signal values, said ranges differing for each subset of said unique coated monomeric particles or aggregated multimers thereof corresponding to each of said multiple analytes; and
   g) calculator means for calculating and correlating a rate of arrival of each of said output signals per unit time from said analyzer means with each said analyte.

2. An optical flow particle analyzer of claim 1 wherein said light source comprises a laser beam generator.

3. An optical flow particle analyzer of claim 1, wherein said optically-defined viewing zone upon which focused light radiation is incident comprises a sheath flow cell for aligning said flowing particles within a central portion of said focused light.

4. An optical flow particle analyzer of claim 1, wherein said lens means comprises a collection lens with a central beam blocker.

5. An optical flow particle analyzer of claim 1, wherein said light detector means comprises a light detector selected from the group consisting of photodiode, photomultiplier, phototransistor and photoresistor detectors.

6. An optical flow particle analyzer of claim 1, further including amplifying means for preamplifying said electrical pulse signals from said single light detector means and applying said preamplified pulse signals to said analyzer means.

7. An optical flow particle analyzer of claim 6, wherein said amplifying means comprises a preamplifier.

8. An optical flow particle analyzer of claim 6, further comprising monitor means for monitoring said preamplified signals.

9. An optical flow particle analyzer of claim 6, wherein said monitoring means for monitoring said preamplified signals comprises an oscilloscope.

10. An optical flow particle analyzer of claim 6, wherein said plurality of single channel analyzers receives preamplified signals and passes as output signals preamplified signals falling within said predetermined ranges of signal values.

11. An optical flow particle analyzer of claim 1, further comprising peak detector means for converting said output signals into digital signals representative of peak heights of said output signals.

12. An optical flow particle analyzer of claim 11, wherein said peak detector means comprises an analog-to-digital signal converter.

13. An optical flow particle analyzer of claim 1, wherein said calculator means comprises a computer.

14. An optical flow particle analyzer of claim 13, wherein said computer includes means for repetitively monitoring the rate of arrival of each output signal from said analyzer means, means for repetitively plotting these rates as a function of time during aggregation reactions of said assay, and means for determining each analyte concentration based on characteristics of each said plot, wherein said plot characteristics are selected from the group consisting of initial rates of change, maximum rates of change, maximum count rate, relative dimer formation with time, differences in dimer:monomer ratio with time, and time intervals.

15. An optical flow particle analyzer for simultaneous assay of multiple analytes in a single fluid sample by a rate-based particle aggregating method, comprising:
 a) a light source;
 b) an optically-defined viewing zone upon which zone focused light from said light source is incident;
 c) means for flowing through said viewing zone a mixture comprising said single fluid sample and a reagent comprising, for each of said multiple analytes, particles of a diameter or refractive index unique for each said analyte, such that each said particle of unique diameter or refractive index or aggregate thereof produces a pulse signal from unidirectional low angle forward light scatter that is distinguishable optically from a pulse signal from unidirectional low angle forward light scatter produced by any other particle of unique diameter or refractive index or aggregate thereof, wherein each said unique particle is coated with a unique composition that corresponds and binds specifically to a corresponding analyte so as to form aggregating coated particle-analyte binding pairs, so that monomeric particles or aggregates formed therefrom flowing through said viewing zone produce discrete pulses of scattered light unique for each said unique coated particle-analyte binding pair or aggregates thereof;
 d) lens means for collecting said pulses of unidirectional low angle forward scattered light;
 e) single light detector means for receiving collected pulses of said unidirectional low angle forward scattered light and converting said pulses into electrical pulse signals, each of said pulse signals being unique for said particle monomers or aggregates thereof corresponding to different analytes;
 f) peak detector means for sampling the peak height values of said electrical pulse signals and outputting peak height signals corresponding thereto; and
 g) calculator means for correlating each said peak height signal with each said analyte.

16. An optical flow particle analyzer of claim 15, wherein said light source comprises a laser beam generator.

17. An optical flow particle analyzer of claim 15, wherein said optically-defined viewing zone upon which focused light radiation is incident comprises a sheath flow cell that aligns said flowing particles in a central portion of said focused light.

18. An optical flow particle analyzer of claim 15, wherein said lens means comprises a collection lens with a central beam blocker.

19. An optical flow particle analyzer of claim 15, wherein said single light detector means comprises a light detector selected from the group consisting of photodiode, photomultiplier, phototransistor and photoresistor detectors.

20. An optical flow particle analyzer of claim 15, further comprising an amplifier means for preamplifying electrical pulse signals from said single light detector means and outputting said preamplified electrical pulse signals to said peak detector means.

21. An optical flow particle analyzer of claim 15, wherein said peak detector means comprises an analog to digital converter that samples the peak height of each said electrical pulse signal and converts said peak height into a digital peak height signal.

22. An optical flow particle analyzer of claim 15, wherein said calculator means comprises a computer.

23. An optical flow particle analyzer of claim 22, wherein said computer includes means for sorting said peak height values by size into histograms, means for selecting peak height intervals bracketing each peak of said histograms, means for repetitively calculating a count rate of each said peak height interval during particle aggregating reactions, means for plotting each of said count rates as a function of time, and, means for determining each said analyte concentration corresponding to each said peak based on characteristics of said plot, wherein said plot characteristics are selected from the group consisting of initial rates of change, maximum rates of change, maximum count rate, relative dimer formation with time, differences in dimer:monomer ratio with time, and time intervals.

24. An optical flow particle analyzer of claim 23 further including means for smoothing said histograms.

* * * * *

UNITED STATES PATENT AND TRADEMARK OFFICE
CERTIFICATE OF CORRECTION

PATENT NO. : 5,286,452
DATED : February 15, 1994
INVENTOR(S) : W. Peter Hansen

It is certified that error appears in the above-identified patent and that said Letters Patent is hereby corrected as shown below:

Column 3, line 57 "tan" should read -- than --.

Column 7, line 38 delete "IgG ( )" and insert -- IgG(--◆--) --.

Column 7, line 39 delete "( )" to read (--□--).

Figure 12:
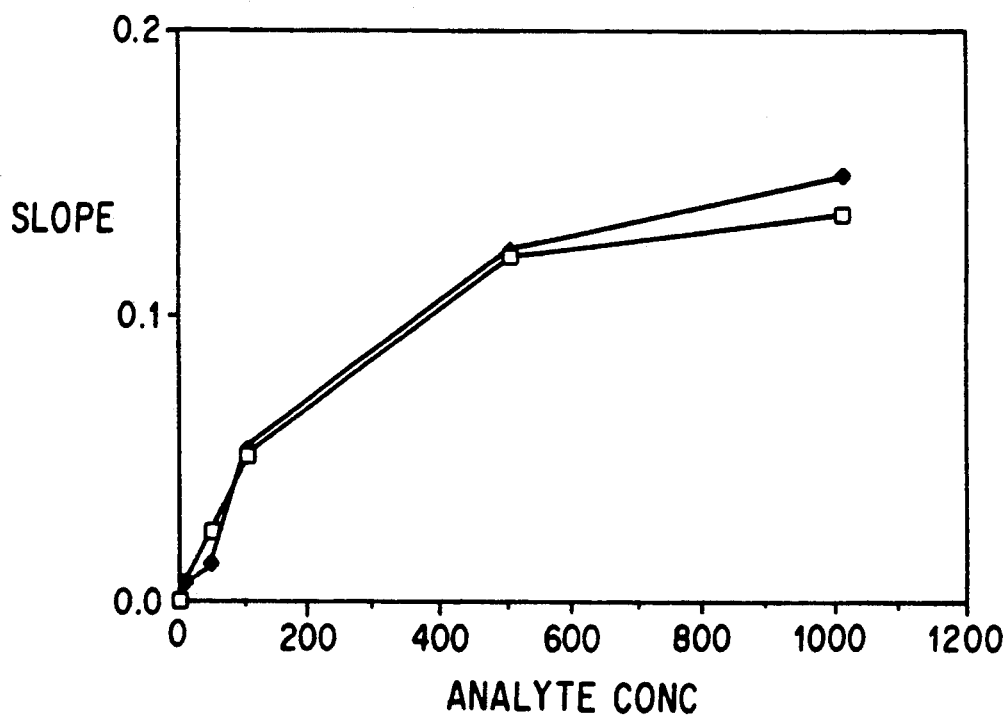
FIG. 12 results of the kinetic assay of the invention applied to immunoglobulin IgG in the presence of IgA ( ), compared to IgG analyzed alone ( ).

Column 7, line 40 after Fig. 12 insert -- shows the --.

Column 7, line 41/42 delete "IgA ( )" and insert -- IgA (--◆--) --.

Column 7, line 42 after the word alone, delete "( )" and insert -- (--□--) --.

Column 7, line 48 delete "1.0 ( )" and insert -- 1.0 (■) --.

Column 7, line 48 delete "25 ( )" and insert -- 25 (●) --.

Column 14, line 60/61 "( in FIG. 13)" should read -- (■ in FIG. 13) --.

Column 14, line 61 "( in FIG. 13)" should read -- (● in FIG. 13) --.

Column 17, table 1, second column, second line, insert ---◆---.

Column 17, table 1, second column, third line, insert ---■---.

UNITED STATES PATENT AND TRADEMARK OFFICE
CERTIFICATE OF CORRECTION

PATENT NO. :  5,286,452
DATED     :  February 15, 1994
INVENTOR(S) :  W. Peter Hansen It is certified that error appears in the above-identified patent and that said Letters Patent is hereby corrected as shown below:

Column 17, table 1, second column, fifth line, insert ---●---.

Column 17, table 1, second column, sixth line, insert ---■---.

Column 17, table 1, second column, eighth line, insert ---●---.

Column 17, table 1, second column, ninth line, insert ---■---.

Column 17, line 31 delete "(   )" and insert (--■--).

Column 18, line 66, delete "claim 6" and insert -- claim 8 --.

Column 20, line 7 delete the word "the".

Signed and Sealed this

First Day of November, 1994

Attest:

BRUCE LEHMAN

Attesting Officer

Commissioner of Patents and Trademarks